US010428116B2

(12) United States Patent
Palmenberg et al.

(10) Patent No.: US 10,428,116 B2
(45) Date of Patent: Oct. 1, 2019

(54) RHINOVIRUS C IMMUNOGENIC PEPTIDES

(71) Applicants: Wisconsin Alumni Research Foundation, Madison, WI (US); Purdue Research Foundation, West Lafayette, IN (US)

(72) Inventors: Ann C. Palmenberg, Madison, WI (US); Marchel Goldsby Hill, Madison, WI (US); Kelly Elizabeth Watters, Madison, WI (US); Michael G. Rossman, Madison, WI (US); Yue Liu, Madison, WI (US)

(73) Assignees: Wisconsin Alumni Research Foundation, Madison, WI (US); Purdue Research Foundation, West Lafayette, IN (US)

( * ) Notice: Subject to any disclaimer, the term of this patent is extended or adjusted under 35 U.S.C. 154(b) by 46 days.

(21) Appl. No.: 15/491,513

(22) Filed: Apr. 19, 2017

(65) Prior Publication Data
US 2017/0305973 A1 Oct. 26, 2017

Related U.S. Application Data

(60) Provisional application No. 62/326,327, filed on Apr. 22, 2016.

(51) Int. Cl.
*C07K 14/005* (2006.01)
*A61K 39/125* (2006.01)
*C12N 7/00* (2006.01)
*C07K 16/10* (2006.01)

(52) U.S. Cl.
CPC .......... *C07K 14/005* (2013.01); *A61K 39/125* (2013.01); *C07K 16/1009* (2013.01); *C12N 7/00* (2013.01); *C07K 2317/34* (2013.01); *C07K 2317/76* (2013.01); *C12N 2770/32722* (2013.01); *C12N 2770/32734* (2013.01)

(58) Field of Classification Search
CPC ...................... C12N 7/00; C12N 15/86; C12N 2770/32334; C12N 2760/16122; C12N 2770/32351; C12N 2770/32734; C12N 2770/32722; C12N 2770/32371; C12N 2770/32762; C12N 2770/32751; C12N 2770/32311; C12N 2770/32721; C12N 2770/32723; C12N 2770/32761; A61K 39/12; A61K 2300/00; A61K 39/125; A61K 2039/525; A61K 38/00; C07K 14/005; C07K 16/1009; C07K 14/085; C07K 14/095; C07K 2317/34; C07K 2317/76

See application file for complete search history.

(56) References Cited

U.S. PATENT DOCUMENTS

| | | | | |
|---|---|---|---|---|
| 2009/0202583 A1* | 8/2009 | Smith | C07K 14/005 | 424/196.11 |
| 2011/0091501 A1* | 4/2011 | Kalnin | A61K 39/145 | 424/227.1 |
| 2017/0290905 A1* | 10/2017 | Castado | A61K 39/125 | |

OTHER PUBLICATIONS

Rathe JA, Naomi SA, Liu X, Tallon LJ, Palmenberg AC, Bochkov YA, Gem JE, Liggett SB. Polyprotein [Rhinovirus C]. GenBank: ACZ67658.1. Dep. Nov. 20, 2010.*
Glanville N, Johnston SL. Challenges in developing a cross-serotype rhinovirus vaccine. Curr Opin Virol. Apr. 2015;11:83-8. Epub Mar. 29, 2015.*
Arden KE, et al. “Frequent detection of human rhinoviruses, paramyxoviruses, coronaviruses, and bocavirus during acute respiratory tract infections.” J. Med. Virol. 78, 1232-1240 (2006).
Acharya R, et al. The three-dimensional structure of foot-and-mouth disease virus at 2.9 A resolution. Nature 337, 709-716 (1989).
Basta HA, et al, Modeling of the human rhinovirus C capsid suggests a novel topography with insights on receptor preference and immunogenicity. Virology 448, 176-184 (2014).
Bartesaghi A, et al. 2.2 A resolution cryo-EM structure of beta-galactosidase in complex with a cell-permeant inhibitor. Science 348, 1147-1151 (2015).
Basavappa R, et al., Role and mechanism of the maturation cleavage of VP0 in poliovirus assembly: structure of the empty capsid assembly intermediate at 2.9 Å resolution. Protein Sci. 3, 1651-1669 (1994).
Bizzintion J, et al. Association between human rhinovirus C and severity of acute asthma in children. Eur. J. Pediatr. 37, 1037-1042 (2011).
Bochkov YA, et al. “Cadherin-related family member 3, a childhood asthma susceptibility gene product, mediates rhinovirus C binding and replication.” Proc. Natl. Acad. Sci. U.S.A. 112, 5485-5490 (2015).
Bochkov YA, et al. Molecular modeling, organ culture and reverse genetics for a newly identified human rhinovirus C. Nature Med. 17, 627-632 (2011).
Drysdale SB, et al. Respiratory outcome of prematurely born infants following human rhinovirus A and C infections. Eur. J. Pediatr. 173, 913-919 (2014).
Filman DJ, et al. Structural factors that control conformational transitions and serotype specificity in type 3 poliovirus. EMBO J. 8, 1567-1579 (1989).
Fricks CE, et al., Cell-induced conformational change in poliovirus: externalization of the amino terminus of VP1 is responsible for liposome binding. J. Virol. 64, 1934-1945 (1990).
Griggs TF, et al. Production, purification, and capsid stability of rhinovirus C types. J. Virol. Methods 217, 18-23 (2015).
Hindiyeh M, et al., Poliovirus mutants at histidine 195 of VP2 do not cleave VP0 into VP2 and VP4. J. Virol. 73, 9072-9079 (1999).
Hogle JM, et al, Three-dimensional structure of poliovirus at 2.9 Å resolution. Science 229, 1358-1365 (1985).
Hogle JM. A 3D framework for understanding enterovirus 71. Nat. Struct. Mol. Biol. 19, 367-368 (2012).
Knowles NJ, et al. Picornaviridae. In: Virus Taxonomy: Classification and Nomenclature of Viruses: Ninth Report of the International Committee on Taxonomy of Viruses (eds King AMQ, Adams MJ, Carstens EB, Lefkowitz EJ). Elsevier (2012).
Ledford RM, et al., Insights into the genetic basis for natural phenotypic resistance of human rhinoviruses to pleconaril. Antiviral Res. 68, 135-138 (2005).

(Continued)

*Primary Examiner* — Rachel B Gill
(74) *Attorney, Agent, or Firm* — Quarles & Brady LLP

(57) ABSTRACT

A peptide comprising the rhinovirus immunogen peptide of the rhinovirus structural protein 1 (VP1) of rhinovirus C and related vaccines and therapeutic compositions is disclosed.

15 Claims, 12 Drawing Sheets
(11 of 12 Drawing Sheet(s) Filed in Color)

Specification includes a Sequence Listing.

(56) References Cited

OTHER PUBLICATIONS

Liu, et al. Structure and inhibition of EV-D68, a virus that causes respiratory illness in children. Science 347, 71-74 (2015).
Liu Y, et al. Sialic acid-dependent cell entry of human enterovirus D68. Nat. Commun. 6, 8865 (2015).
Luo M, et al. The atomic structure of Mengo virus at 3.0 A resolution. Science 235, 182-191 (1987).
Miller EK, et al. "Human rhinovirus C associated with wheezing in hospitalised children in the Middle East," J. Clin. Virol. 46, 85-89 (2009).
Piralle A, et al. Clinical severity and molecular typing of human rhinovirus C strains during a fall outbreak affecting hospitalized patients. J. Clin. Virol. 45, 311-317 (2009).
Rogers JM, Diana GD, McKinlay MA. Pleconaril. A broad spectrum antipicornaviral agent. Adv. Exp. Med. Biol. 458, 69-76 (1999).
Rossmann MG, et al. "Structure of a human common cold virus and functional relationship to other picornaviruses," Nature 317, 145-153 (1985).
Rossmann MG. The canyon hypothesis. Hiding the host cell receptor attachment site on a viral surface from immune surveillance. J. Biol. Chem. 264, 14587-14590 (1989).
Rossmann MG, et al. Picornavirus-receptor interactions. Trends Microbiol. 10, 324-331 (2002).
Simmonds et al. "Proposals for the classification of human rhinovirus species C into genotypically assigned types." 2010 J. Gen. Virol. 91:2409-2419.
Smyth M, Pettitt T, Symonds A, Martin J. Identification of the pocket factors in a picornavirus. Arch. Virol. 148, 1225-1233 (2003).
Zhao R, et al. Human rhinovirus 3 at 3.0 Å resolution. Structure 4, 1205-1220 (1996).

* cited by examiner

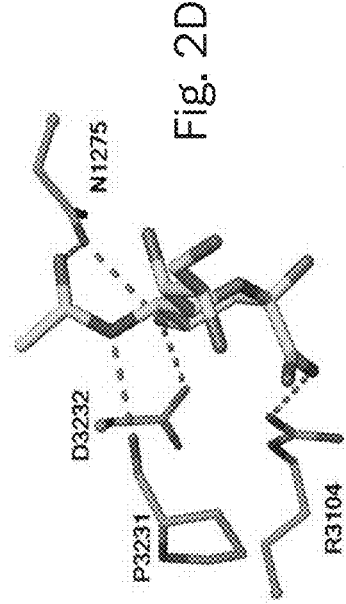
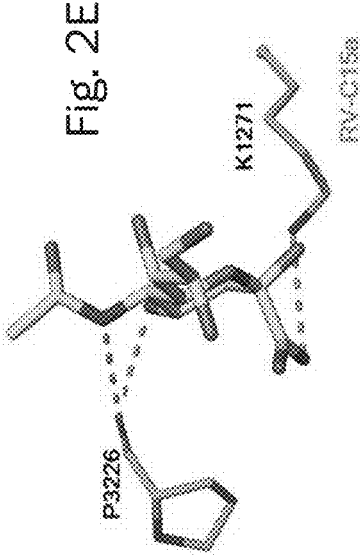
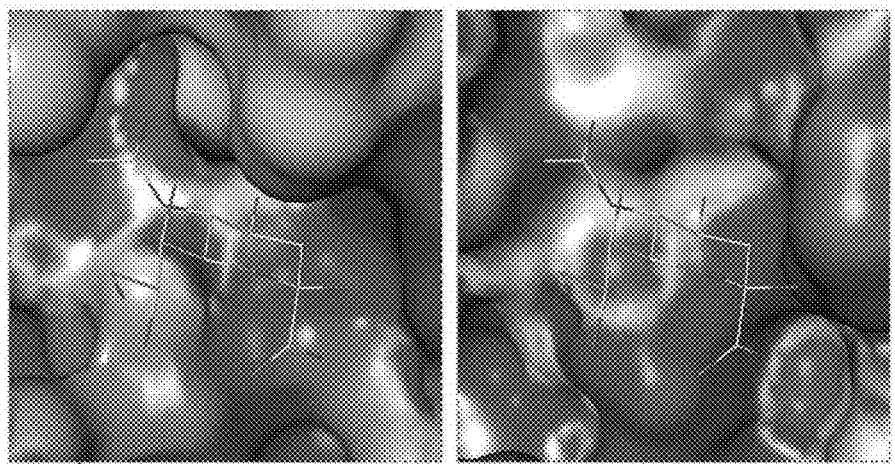
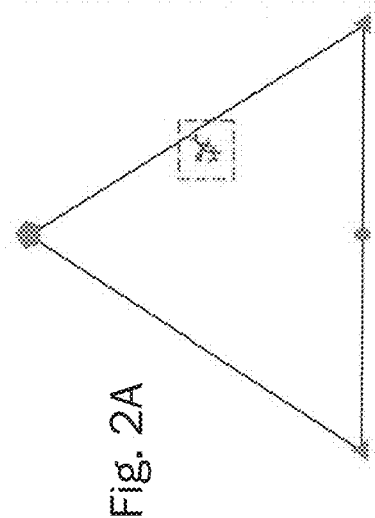

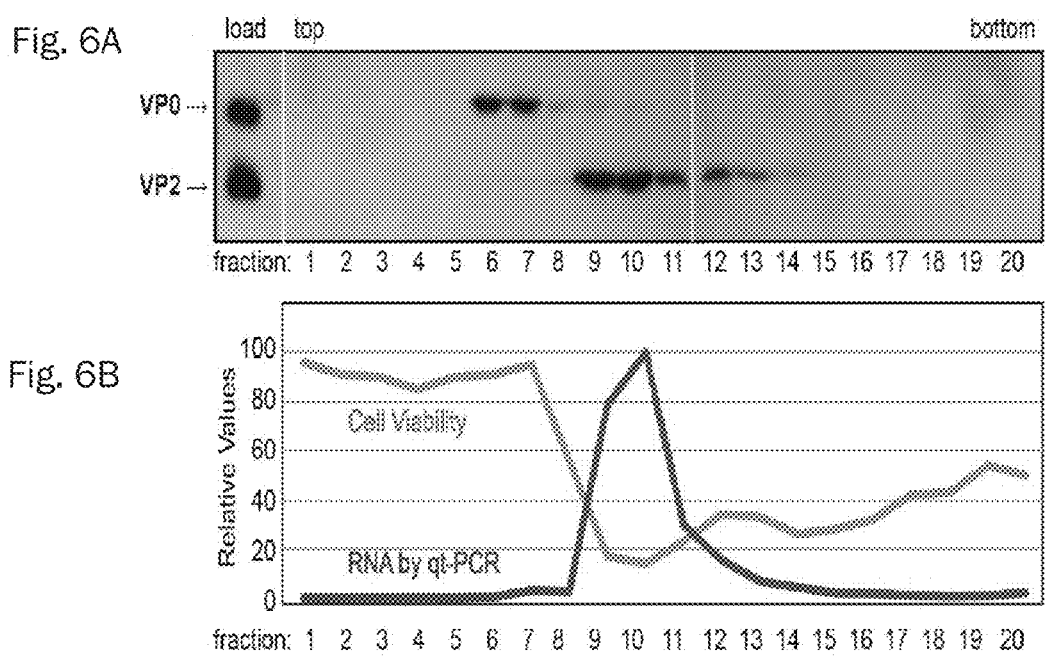

A. C15 (partial) protein VP1 sequence (GenBank: GU219984)

....ATQYTHKYSTNYHYKPNSSGPDEHVLKDRHFIKTRPLISSA-cooh positions 252, 266, 279 marked over sequence (SEQ ID NO:129)

Boldface peptide seq is encoded by genome bases: 3062-3106 inclusive.

B. C15 (partial) protein VP2 sequence (GenBank: GU219984)

....VKVNVGYDHTHPGQSGHQIRGPSQSNDRSGGKPDEDPLF....

positions 155, 167 marked over sequence (SEQ ID NO:130)

Boldface peptide seq is encoded by genome bases: 1271-1309 inclusive.

RHINOVIRUS C IMMUNOGENIC PEPTIDES

CROSS REFERENCE TO RELATED APPLICATIONS

This application claims benefit of U.S. Patent Application 62/326,327 filed Apr. 22, 2016, which is incorporated herein by reference.

STATEMENT REGARDING FEDERALLY SPONSORED RESEARCH/DEVELOPMENT

This invention was made with government support under AI104317 awarded by the National Institutes of Health. The government has certain rights in the invention.

BACKGROUND

The Picornaviridae family includes a variety of small, non-enveloped, icosahedral viruses with positive-strand RNA genomes[1]. Many picornaviruses (e.g., rhinoviruses, polioviruses, coxsackieviruses, enterovirus A71, enterovirus D68) that infect humans and cause high morbidity belong to the Enterovirus genus (EV)[1]. A number of these viruses have been structurally characterized by X-ray crystallography[2,3,4,5], establishing the general mechanisms for virus infection and for the development of effective anti-EV therapeutics. Nevertheless, rhinovirus C (RV-C), a newly discovered species among the EVs, remains enigmatic.

RV-C viruses (55 types), together with RV-A and RV-B viruses (~100 types), are the leading cause of common colds. However, the RV-C lead to more severe respiratory infections among children than any other known rhinoviruses[6]. In contrast to other RV, the RV-C utilize cadherin related family member 3 (CDHR3) as a cellular receptor[7]. This childhood asthma susceptibility gene product is expressed in the human lower respiratory tract[8]. In line with this etiology, RV-Cs cause a significantly higher rate of lower respiratory tract infections in children than in adults[9] and are directly associated with childhood asthma exacerbations[10]. Similar to influenza, RV-C infections peak in winter months. Currently, there are no vaccines or effective antiviral treatments available.

RV-C isolates have been refractory to structural characterization since their discovery in 2006[11] because of an inability to infect standard tissue culture (e.g., HeLa)[12]. Only modeled structures, based on amino acid sequence comparisons, have been available to aid biological investigations[12,13,14]. However, with recent advances in direct electron detection[15] and image processing approaches[16,17] single-particle cryo-electron microscopy (cryo-EM) has now emerged as a powerful method for determining near atomic resolution (better than 4 Å) structures of macromolecular assemblies[18]. Cryo-EM requires only limited amount of sample without intensive purification, offering advantages over X-ray crystallography in structural studies of samples that are difficult to produce.

Picornavirus capsids are assembled from 60 copies of biological protomers, each composed of four proteins, VP1, VP2, VP3 and VP4[2]. The three large surface polypeptides, VP1, VP2 and VP3 are folded into eight-stranded antiparallel "jelly rolls." During the assembly process, autocatalytic cleavage of precursor VP0 into VP2 and VP4 in the presence of viral RNA results in the formation of full infectious virions[19]. The arrangement of jelly rolls in the virions exhibits pseudo T=3 icosahedral symmetry with an outer diameter of about 300 Å[2,3]. The internal surface of the capsid is lined by the 60 copies of VP4. A surface depression or canyon[2], encircling each five-fold axis, is frequently the receptor binding site for many EV[20]. Amino acid residues located on the outer surface of the virus but not specifically within this canyon are typically involved in forming immunogenic sites recognized by neutralizing antibodies. The canyon allows only limited access to these antibodies[21]. In many EV, a hydrophobic pocket within the VP1 jelly roll and situated underneath the canyon floor is occupied by a fatty-acid like molecule, or "pocket factor,"[22,23] that regulates the conformational states of the virus during cell entry[24]. Capsid-binding reagents that replace the pocket factor within VP1 are effective antiviral therapeutics against many EV[25], but not RV-C[14].

In the Examples below we report atomic resolution cryo-EM structures of the full and native empty particles (NEP) of the cell-adapted RV-C15a strain. These structures highlight novel immunogenic surfaces, a probable binding site for the glycosylated CDHR3 receptor molecule and the requirements for antiviral compound resistance. The novel immunogenic peptides identified in the work reported herein are useful targets for therapeutic antibodies and related therapeutics.

DESCRIPTION OF THE DRAWINGS

This patent application file contains at least one drawing executed in color. Copies of this patent or patent application publication with color drawing(s) will be provided by the Office upon request and payment of the necessary fee.

FIGS. 2A-2E identifies a potential binding site for glycans on the RV-C receptor. (A) A triangle indicates an icosahedral asymmetric unit. A red rectangle (dash line) outlines the limit of the sialic acid binding site shown in (B) and (C). Surface electrostatic potential of EV-D68 (PDB accession number 5BNO) (B) and RV-C15a (C) is represented with a scale of −8 kT/e (red) to 8 kT/e (blue). (D) and (E) The sialic acid (yellow) interacts with surrounding residues on EV-D68 (green) and RV-C15a (cyan). Red dash lines indicate polar interactions. Oxygen and nitrogen atoms are colored red and blue, respectively.

FIGS. 6A and 6B show the characterization of two forms of RV-C15a particles. A sample of RV-C15a was sedimented through a sucrose gradient. Fractions (1 ml) were collected (from the top) and then probed for VP2/VP0 content by Western blot analyses (A) using mouse anti-RV-C15-VP2. These fractions were also tested for infectivity according to cytopathic effect (B), and for RNA content by qRT-PCR (B).

FIG. 11 is an atomic resolution structure of rhinovirus C15a.

FIGS. 12A-12B shows peptide sequences chosen for peptide antibody analysis in the C15a VP1 (A) and VP2 (B) proteins.

DESCRIPTION OF THE INVENTION

In General

Figure 1A:
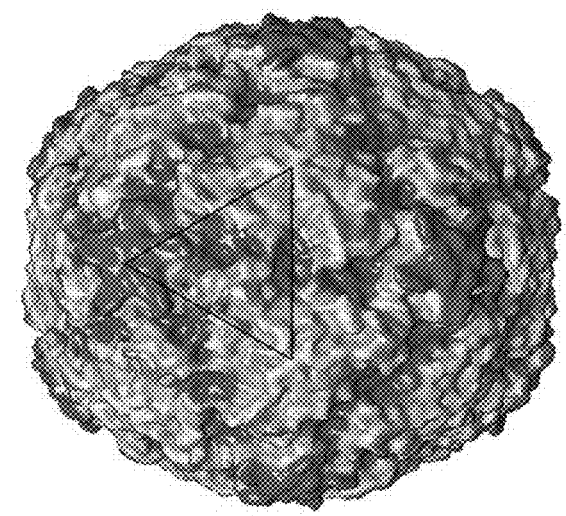
FIGS. 1A-1C identify the spiky structure of RV-C15a. A 10 Å resolution density map of RV-B14 (PDB accession number 4RHV) (A) and RV-C15a (B) calculated based on the respective coordinates is color-coded based on radial distance (A) to the virus center. A black triangle indicates an icosahedral asymmetric unit on each of the two viruses. A rectangle (black dash line) outlines the limit of a close up view of a "finger" in (C). Residues that form the finger region, which are fitted into the EM map densities (grey), are shown as Cα backbones and colored blue (VP1 residues) and green (VP2 residues).

In the Examples below Applicants report and analyze an atomic resolution structure of the rhinovirus (RV) C15a virus virion structure. Unexpectedly, in view of previous sequencing and modeling experimental efforts, a small sequence segment proximal to the carboxyl tail of the virus protein VP1 ("Virion Protein 1") was found to have extensive surface exposure. This particular segment is not present in the sequences of RV-A and RV-B, and, therefore, the segment was not anticipated to have surface and/or immunogenic properties.

Using their knowledge of this new putative epitope, Applicants produced two synthetic peptides. One peptide included the new potentially immunogenic segment of the 15 residue C15 VP1 sequence and the other included a previously identified, possibly immunogenic 13 residue site nearby on the virion surface that was contributed by the viral VP2 capsid protein. These peptides were each inoculated into five mice. When Applicants tested the resulting murine polyclonal sera in Western assays, the VP1 peptide, but not the VP2 peptide, was found to have elicited an immune response in all five animals.

When these sera were tested in micro-neutralization assays, three of the five sera elicited to the predicted VP1 protein were able to neutralize the virus itself. None of the mice immunized with the VP2 peptide were reactive with virus, or produced neutralizing sera.

Therefore, Applicants have defined the reactive immunogenicity of an RV-C15 virus VP1 segment that can elicit protective, neutralizing antibodies. This segment is unique in structure and sequence (i.e. defining the dominant immunology) to the RV-C species of viruses. Knowledge of this segment allows Applicants to predict a corresponding segment in other members of the RV-C class. Peptide or virus reagents which elicit antibodies to this segment are likely vaccine and antiviral targets.

Immunogenic Peptides and Compositions of the Present Invention

In one embodiment, the present invention is a composition comprising the immunogenic peptides described below. In a preferred embodiment, the invention is a peptide comprising a Rhinovirus-C structural protein 1 (VP1) rhinovirus immunogen peptide, wherein the peptide does not comprise flanking sequence with which the amino acids are contiguous in a naturally occurring rhinovirus. By "Rhinovirus C immunogen peptide" we mean to include the peptide as defined in RV-C15 and all other known and unknown strains of Rhinovirus C.

The Examples below define the immunogen peptide of RV-C15 as amino acids 252-266 (SEQ ID NO: 1 [YKPNSSGPDEHVLKD]) of the VP1 protein (see also FIG. 12). Table 1, below, lists the corresponding peptide in all other known rhinovirus C isolates. One of skill in the art would understand how to derive the corresponding sequence from currently unknown strains by comparing the new sequence to the table below.

TABLE 1

Peptide sequences in naturally occurring rhinovirus C isolates which are in structurally analogous capsid positions to RV-C15 VP1 peptide: YKPNSSGPDEHVLKD (SEQ ID NO: 1)

| RV Species | Type[a] | GenBank[b] example | N-flanking[c] VP1 region | Structurally analogous[ce] VP1 peptide sequence | COOH-flanking[c] VP1 region |
|---|---|---|---|---|---|
| C | 01 | EF077279 | TNYN (SEQ ID NO: 2) | KQKPDSGGQVEP (SEQ ID NO: 3) | KHFLNTRNDIKNL (SEQ ID NO: 4) |
| C | 02 | EF077280 | PNYH (SEQ ID NO: 5) | TNKGSTTELEE (SEQ ID NO: 6) | KHYINTRTTIKTA (SEQ ID NO: 7) |

TABLE 1-continued

Peptide sequences in naturally occurring rhinovirus C isolates which are in structurally analogous capsid positions to RV-C15 VP1 peptide: YKPNSSGPDEHVLKD (SEQ ID NO: 1)

| RV Species | Type[a] | GenBank example[b] | N-flanking VP1 region[c] | Structurally analogous VP1 peptide sequence[ce] | COOH-flanking VP1 region[c] |
|---|---|---|---|---|---|
| C | 03 | EF186077 | TNYN (SEQ ID NO: 2) | KPKTSGSTELEP (SEQ ID NO: 8) | KHFFKYRQDITSI (SEQ ID NO: 9) |
| C | 04 | EF582385 | TNYH (SEQ ID NO: 10) | VKKPDDTTGLLIQ (SEQ ID NO: 11) | KHFINHRTDIKTA (SEQ ID NO: 12) |
| C | 05 | EF582386 | TNYN (SEQ ID NO: 2) | RRVNPNSEDSTLTR (SEQ ID NO: 13) | DHYIKTRATVTTA (SEQ ID NO: 14) |
| C | 06 | EF582387 | TNYN (SEQ ID NO: 2) | KPKTKGSNELEP (SEQ ID NO: 15) | KHFLKYRDDITSI (SEQ ID NO: 16) |
| C | 07 | JN798559 | TNYN (SEQ ID NO: 2) | VIKKGTTSDLEQ (SEQ ID NO: 17) | KHFLTYRTDITNV (SEQ IDNO: 18) |
| C | 08 | GQ223227 | TNYH (SEQ ID NO: 10) | YKAPDATPQQLES (SEQ ID NO: 19) | RHFMKFREQIKNV (SEQ ID NO: 20) |
| C | 09 | GQ223228 | TNYH (SEQ ID NO: 10) | TPTGASDGTLKE (SEQ ID NO: 21) | KHYLKHRDDIKNL (SEQ ID NO: 22) |
| C | 10 | GQ323774 | TNYN (SEQ ID NO: 2) | KPETEGSNILIQ (SEQ ID NO: 23) | KHFLEHRADITTL (SEQ ID NO: 24) |
| C | 11 | EU840952 | TNYN (SEQ ID NO: 2) | RKVSDDDSTLTR (SEQ ID NO: 25) | DHYIETRASVKTA (SEQ ID NO: 26) |
| C | 12 | JF317017 | TNYH (SEQ ID NO: 10) | YRTGTEGNYTLKN (SEQ ID NO: 27) | RHFIQHRNNIKGL (SEQ ID NO: 28) |
| C | 13 | HM236908 | VNYN (SEQ ID NO: 29) | IAKPNSGGLLEQ (SEQ ID NO: 30) | KHFLKHRPDIKSA (SEQ ID NO: 31) |
| C | 14 | HM236911 | PNYH (SEQ ID NO: 32) | TTAPEGGGLLKE (SEQ ID NO: 33) | EHYFKFRENIKTA (SEQ ID NO: 34) |
| C | 15 | GU219984 | TNYH (SEQ ID NO: 10) | YKPNSSGPDEHVLKD (SEQ ID NO: 1) | RHFIKTRPLISSA (SEQ ID NO: 35) |
| C | 15 | JF317014 | TNYH (SEQ ID NO: 10) | YKPNSSGPDQHVLED (SEQ ID NO: 36) | RHFIKTRPHISSA (SEQ ID NO: 37) |
| C | 15 | JN837688 | TNYH (SEQ ID NO: 10) | YKPNADEHILED (SEQ ID NO: 38) | RHFIKTRPLISSA (SEQ ID NO: 39) |
| C | 17 | JN815240 | TNYH (SEQ ID NO: 10) | VPDSNETDGLKE (SEQ ID NO: 40) | KHFIKPREHIKNV (SEQ ID NO: 41) |
| C | 18 | HM236918 | TNYH (SEQ ID NO: 10) | YKEEESEQNLKD (SEQ ID NO: 42) | RHFMEFRREIKTT (SEQ ID NO: 43) |
| C | 18 | HM236948 | TNYH (SEQ ID NO: 10) | KEENESEQNLKD (SEQ ID NO: 44) | RHFMEFRREIKTT (SEQ ID NO: 45) |
| C | 19 | EU840728 | PNYH (SEQ ID NO: 32) | TKVNDTQVLKE (SEQ ID NO: 46) | EHYIKFRESPRTI (SEQ ID NO: 47) |
| C | 20d | HM236923 | TNYN (SEQ ID NO: 2) | KKKVPTDPNNHELTK (SEQ ID NO: 48) | VHFLKPRTEIKTT (SEQ ID NO: 49) |
| C | 21 | HM236903 | TNYN (SEQ ID NO: 2) | SVKSGTLNDLEQ (SEQ ID NO: 50) | KHFLTHRPDITTA (SEQ ID NO: 51) |
| C | 22 | JN621242 | TNYN (SEQ ID NO: 2) | NVKDQGTKALEQ (SEQ ID NO: 52) | KHFLVSRTDIKNV (SEQ ID NO: 53) |
| C | 23 | KJ675506 | TNYH (SEQ ID NO: 10) | YKADDNTSTLTD (SEQ ID NO: 54) | RHFLTPRDTITTA (SEQ ID NO: 55) |
| C | 24 | HM236939 | TNYY (SEQ ID NO: 56) | FKSKENENILVP (SEQ ID NO: 57) | KHFIKPRANIKNV (SEQ ID NO: 58) |

TABLE 1-continued

Peptide sequences in naturally occurring rhinovirus C isolates which are in structurally analogous capsid positions to RV-C15 VP1 peptide: YKPNSSGPDEHVLKD (SEQ ID NO: 1)

| RV Species | Type[a] | GenBank example[b] | N-flanking VP1 region[c] | Structurally analogous VP1 peptide sequence[ce] | COOH-flanking VP1 region[c] |
|---|---|---|---|---|---|
| C | 25 | HQ123440 | TNYH (SEQ ID NO: 10) | YKPDGEGHALTD (SEQ ID NO: 59) | RHFIQKRNNIKNV (SEQ ID NO: 60) |
| C | 26 | JX193796 | TNYH (SEQ ID NO: 10) | TKADESGNLKE (SEQ ID NO: 61) | EHYFRFRRDIKGI (SEQ IDNO: 62) |
| C | 27 | HM236906 | TNYN (SEQ ID NO: 2) | RKLADNTLKV (SEQ ID NO: 63) | DHYITTRPTVKTA (SEQ ID NO: 64) |
| C | 28 | JN798569 | TNYH (SEQ ID NO: 10) | YKEKDASEDTLKS (SEQ ID NO: 65) | RHFMEFRTAIKNV (SEQ ID NO: 66) |
| C | 29 | HM236949 | TNYN (SEQ ID NO: 2) | RKVRDDSHDLEK (SEQ ID NO: 67) | THFIKTRNSIKTA (SEQ ID NO: 68) |
| C | 29d | HM236966 | TNYN (SEQ ID NO: 2) | KKKVPTDPNNHELTK (SEQ ID NO: 48) | VHFLKPRTEIKTT (SEQ ID NO: 69) |
| C | 30 | HM236968 | TNYP (SEQ ID NO: 70) | YKANDTSPLEDV (SEQ ID NO: 71) | RHFIKTRNPIWNV (SEQ ID NO: 72) |
| C | 31 | HM236964 | TNYH (SEQ ID NO: 10) | YKAPGNAQELKD (SEQ ID NO: 73) | RHFMQFRKQIKN (SEQ ID NO: 74) |
| C | 32 | JN798581 | VNYN (SEQ ID NO: 29) | IPKTGSTTSELEQ (SEQ ID NO: 75) | KHFLIPREDIKNV (SEQ ID NO: 76) |
| C | 33 | HM236934 | PNYH (SEQ ID NO: 77) | VPIEGGSGNLKE (SEQ ID NO: 78) | EHYFKFRNDIKAT (SEQ ID NO: 79) |
| C | 34 | JF436926 | TNYN (SEQ ID NO: 2) | KRKQPTNPDNHELTK (SEQ ID NO: 80) | VHFLKPRPGDSIK (SEQ ID NO: 81) |
| C | 35 | JF436925 | PNYH (SEQ ID NO: 32) | VNIGETKELTE (SEQ ID NO: 82) | RHYLKPRDDITTV (SEQ ID NO: 83) |
| C | 36 | JN541267 | PNYH (SEQ ID NO: 32) | TRTGENNGTLEE (SEQ ID NO: 84) | KHYIKTRTNIKTF (SEQ ID NO: 85) |
| C | 37 | JF416321 | TNYH (SEQ ID NO: 10) | IRDGDQGMLKQ (SEQ ID NO: 86) | KHYFKYRDDIKNF (SEQ ID NO: 87) |
| C | 38 | JF416322 | TNYN (SEQ ID NO: 2) | RRVYPDSADST (SEQ ID NO: 88) | KHYITTRESIKTA (SEQ ID NO: 89) |
| C | 38 | JN837691 | TNYN (SEQ ID NO: 2) | RRVYPDSADSTLTK (SEQ ID NO: 90) | DHYITTRESIKTA (SEQ ID NO: 91) |
| C | 39 | JN205461 | VNYN (SEQ ID NO: 29) | VIKTGTTTGELEQ (SEQ ID NO: 92) | KHFLVARPDIKNV (SEQ ID NO: 93) |
| C | 40 | JF781505 | PNYH (SEQ ID NO: 32) | TRKNNTSELEE (SEQ ID NO: 94) | KHYIKTRETIKTA (SEQ ID NO: 95) |
| C | 41 | JN798565 | TNYH (SEQ ID NO: 10) | YKADENSPLKD (SEQ ID NO: 96) | RHFITTRESIKNV (SEQ ID NO: 97) |
| C | 42 | JF416320 | TNYH (SEQ ID NO: 10) | YKKGDALE (SEQ ID NO: 98) | RHFIHTRRHIKIL (SEQ ID NO: 99) |
| C | 42 | JQ994500 | TNYH (SEQ ID NO: 10) | YKKEDTTLEDRHFI (SEQ ID NO: 100) | QHRDGIKILQNA (SEQ ID NO: 101) |
| C | 43 | JN815249 | TNYN (SEQ ID NO: 2) | KIKVEATKELEQ (SEQ ID NO: 102) | KHFLKPRQDIRNV (SEQ ID NO: 103) |
| C | 43 | JN837687 | TNYN (SEQ ID NO: 2) | KIKVETTKELEQ (SEQ ID NO: 104) | KHFLKPRQDIRNA (SEQ ID NO: 105) |
| C | 44 | JF416310 | TNYH (SEQ ID NO: 10) | FKTVHEGKNILKD (SEQ ID NO: 106) | RHFIIPRSNILGL (SEQ ID NO: 107) |

TABLE 1-continued

Peptide sequences in naturally occurring rhinovirus C isolates which are in structurally analogous capsid positions to RV-C15 VP1 peptide: YKPNSSGPDEHVLKD (SEQ ID NO: 1)

| RV Species | Type[a] | GenBank example[b] | N-flanking VP1 region[c] | Structurally analogous VP1 peptide sequence[c,e] | COOH-flanking VP1 region[c] |
|---|---|---|---|---|---|
| C | 45 | JN837686 | TNYN (SEQ ID NO: 2) | RKVNETTTDLTK (SEQ ID NO: 108) | RHYIQKRTSVKSA (SEQ ID NO: 109) |
| C | 45 | JF416308 | THYN (SEQ ID NO: 2) | REVNETTTDLTK (SEQ ID NO: 110) | RHYIQKRTSVKSA (SEQ ID NO: 111) |
| C | 46 | JF416318 | PNYH (SEQ ID NO: 32) | VPTQANDGTLEE (SEQ ID NO: 112) | RHYFKFRGDIKTA (SEQ ID NO: 113) |
| C | 47 | JF519760 | PNYH (SEQ ID NO: 32) | TNKGTTTELEE (SEQ ID NO: 114) | KHYIKTRESIKTV (SEQ ID NO: 115) |
| C | 48 | JF519762 | TDYH (SEQ ID NO: 116) | IPVEGGSGGLRE (SEQ ID NO: 117) | RHYFTFREDIKTA (SEQ ID NO: 118) |
| C | 49 | JF907574 | TNYH (SEQ ID NO: 10) | VKKPGDDTGLLIQ (SEQ ID NO: 119) | KHFIKPRGDIKTA (SEQ ID NO: 120) |
| C | 50 | KF688606 | PNYH (SEQ ID NO: 32) | TKNASNENVLEE (SEQ ID NO: 121) | KHYMKHRTDIKTA (SEQ ID NO: 122) |
| C | 51 | JF317015 | TNYH (SEQ ID NO: 10) | IKDGEQGMLRQ (SEQ ID NO: 123) | RHYFKHRGDIKNL (SEQ ID NO: 124) |
| C | 54 | KP282614 | TNYN (SEQ ID NO: 2) | RKVNSTSHDLTK (SEQ ID NO: 125) | THFIKTRDSIKTA (SEQ ID NO: 126) |
| C | 55 | KR997885 | PNYH (SEQ ID NO: 32) | LPKEGSNDLTE (SEQ ID NO: 127) | KHYLDSRNDITTA (SEQ ID NO: 128) |

[a] "Type" is a designation assigned by the International Committee on the Taxonomy of Viruses (ICTV) to bin phylogenetically similar isolates. The criteria are based on protein and nucleic acid sequence similarity in the VP1 and VP2 genes. (1)
[b] NCBI GenBank entry encoding this sequence.
[c] VP1 protein sequences on the N-terminus and COOH terminus of the structurally analogous VP1 immunogenic sequence are shown for context. Neither of the context flanking sequences is required for the external VP1 loop to exhibit immunogenicity when encoded in the virus capsid, proper. Maximum analogous length is 15 amino acids (aa); minimum length is 8 aa, average/mode length is 12 aa.
[d] These sequences are identical. HM236966 is potentially misclassified in the literature as a type 29. It should be a type 20.
[e] Alphabetical list of the 59 structurally analogous VP1 sequence segments in this table: FKSKENENILVP (SEQ ID NO: 57), FKTVHEGKNILKD (SEQ ID NO: 106), IAKPNSGGLLEQ (SEQ ID NO: 30), IKDGEQGMLRQ (SEQ ID NO: 123), IPKTGSTTSELEQ (SEQ ID NO: 75), IPVEGGSGGLRE (SEQ ID NO: 117), IRDGDQGMLKQ (SEQ ID NO: 86), KEENESEQNLKD (SEQ ID NO: 44), KIKVEATKELEQ (SEQ ID NO: 102), KIKVETTKELEQ (SEQ ID NO: 104), KKKVPTDPNNHELTK (SEQ ID NO: 48), KPETEGSNILIQ (SEQ ID NO: 23), KPKTKGSNELEP (SEQ ID NO: 15), KPKTSGSTELEP (SEQ ID NO: 8), KQKPDSGGQVEP (SEQ ID NO: 3), KRKQPTNPDNHELTK (SEQ ID NO: 80), LPKEGSNDLTE (SEQ ID NO: 127), NVKDQGTKALEQ (SEQ ID NO: 52), REVNETTTDLTK (SEQ ID NO: 110), RKLADNTLKV (SEQ ID NO: 63), RKVNETTTDLTK (SEQ ID NO: 108), RKVNSTSHDLTK (SEQ ID NO: 125), RKVRDDSHDLEK (SEQ ID NO: 67), RKVSDDDSTLTR (SEQ ID NO: 25), RRVNPNSEDSTLTR (SEQ ID NO: 13), RRVYPDSADST (SEQ ID NO: 88), RRVYPDSADSTLTK (SEQ ID NO: 90), SVKSGTLNDLEQ (SEQ ID NO: 50), TKADESGNLKE (SEQ ID NO: 61), TKNASNENVLEE (SEQ ID NO: 121), TKVNDTQVLKE (SEQ ID NO: 46), TNKGSTTELEE (SEQ ID NO: 6), TNKGTTTELEE (SEQ ID NO: 114), TPTGASDGTLKE (SEQ ID NO: 21), TRKNNTSELEE (SEQ ID NO: 94), TRTGENNGTLEE (SEQ ID NO: 84), TTAPEGGGLLKE (SEQ ID NO: 33), VIKKGTTSDLEQ (SEQ ID NO: 17), VIKTGTTTGELEQ (SEQ ID NO: 92), VKKPDDTTGLLIQ (SEQ ID NO: 11), VKKPGDDTGLLIQ (SEQ ID NO: 119), VNIGETKELTE (SEQ ID NO: 82), VPDSNETDGLKE (SEQ ID NO: 40), VPIEGGSGNLKE (SEQ ID NO: 73), VPTQANDGTLEE (SEQ ID NO: 112), YKADDNTSTLTD (SEQ ID NO: 54), YKADENSPLKD (SEQ ID NO: 96), YKANDTSPLEDV (SEQ ID NO: 71), YKAPDATPQQLES (SEQ ID NO: 19), YKAPGNAQELKD (SEQ ID NO: 78), YKEEESEQNLKD (SEQ ID NO: 42), YKEKDASEDTLKS (SEQ ID NO: 65), YKKEDTTLEDRHFI (SEQ ID NO: 100), YKKGDALE (SEQ ID NO: 98), YKPDGEGHALTD (SEQ ID NO: 59), YKPNADEHILED (SEQ ID NO: 38), YKPNSSGPDEHVLKD (SEQ ID NO: 1), YKPNSSGPDQHVLED (SEQ ID NO: 36), YRTGTEGNYTLKN (SEQ ID NO: 27)
1. Simmonds, P., C. McIntyre, C. Savolainen-Kopra, C. Tapparel, I. M. Mackay, and T. Hovi. 2010. Proposals for the classification of human rhinovirus species C into genotypically assigned types. J. Gen. Virol. 91: 2409-2419.

In one preferred version of the present invention, a nucleic acid encoding the peptide is part of an expression vector. In one version, the vector comprises a peptide operably linked to a transcriptional regulatory element wherein the peptide encodes the epitope described above. Preferable expression vectors include those listed in the GenScript web site: www.jpt.com/products/peptide-conjugates-klh-bsa/.

In another version, the present invention is a cell comprising the vector or peptide described above. In another version, the cell expresses the protein. In another version, the present invention is the peptide expressed by the cell.

The present invention includes a vaccine comprising the rhinovirus immunogen peptide described above, preferably including a pharmaceutically acceptable carrier. Preferably, the vaccine comprises an adjuvant.

In one embodiment, the vaccine is a peptide vaccine. Peptide vaccines are useful in eliciting an immunogenic response but are sometimes found to not stimulate cells in exactly the same way as a traditional vaccine. For example, a peptide vaccine may not cause a thymus cell, or T-cell, to react as much as other vaccines. To combat this, the peptide vaccine can be bound to a carrier protein or peptide to improve cell interaction. A suitable carrier will present the epitope peptide in a way that improves the immunogenicity of the peptide and allows the enhanced production of antibodies against the peptide. One of skill in the art would understand the construction of a peptide vaccine. Good information on peptides and their administration as vaccines (or to raise antibodies), comes from the GenScript web site: www.jpt.com/products/peptide-conjugates-klh-bsa/.

In one version, the present invention is a pharmaceutical composition comprising the immunogen peptide described above, preferably combined with pharmaceutical carriers.

In another version, the present invention is an antibody or antibody binding fragment thereof which binds to the epitope comprising the immunogen peptide described above. Preferably, the antibody is neutralizing against rhinovirus C.

Preferably, the antibody inhibits rhinovirus infection in a subject, such as a human or animal subject. By "inhibits," we mean that infection is decreased or inhibited or that the rate of infection is reduced. One may wish to give the pharmaceutical preparation of the present invention in a prophylactic manner.

In a preferred embodiment, the antibody ameliorates symptoms of rhinovirus C infection in a subject, wherein the antibody is administered to a subject after infection with the rhinovirus.

Monoclonal antibody therapies (immunotherapy) are now quite common in cancer treatment. For example, common monoclonal antibody therapies for managing colon cancer are Bevacizumab (Avastin), Cetuximab (Erbitux), and Panitumumab (Vectibix). There are many more examples. The process is described on the ACS web site at www.cancer.org/treatment/treatmentsandsideeffects/treatmenttypes/immunotherapy/immunotherapy-monoclonal-antibodies.

In one embodiment, the antibody is a monoclonal antibody. In another embodiment, the antibody is a polyclonal antibody.

In a preferred version of the present invention, the monoclonal antibody recognizes VP1 of rhinovirus C, wherein the epitope that binds or is recognized by said antibody is within SEQ ID NO:1 or the other immunogen peptides listed in Table 1.

The present invention is also a hybridoma cell line that produces a monoclonal antibody as described above.

In another embodiment, the present invention is an immunogenic composition comprising an isolated preparation of empty Rhinovirus C particles, as described below in the Examples. In a preferred embodiment, the preparation is useful as a vaccine and contains no live virus. In another embodiment, the isolated preparation is combined with an element selected from the group consisting of pharmaceutical carriers and adjuvants.

Methods of Eliciting an Immune Response

In one embodiment, the present invention is a method of eliciting an immune response against rhinovirus C in a subject. Typically, the method comprises administering to the subject the immunogen peptide or a vaccine as described above.

A sufficient immune response can typically be measured as follows: Blood serum from an inoculated individual can be tested as per FIG. 13, for an elicited antibody reaction which protects tissue culture cells from RV-C infection. This assay also gives a numerical titer of the antibody strength. In the field, a titer of >1:10 (i.e. 10 fold dilution of antibody sample is protective) is generally considered "protective" in a vaccine context for humans or animals.

In one version of the invention, one may wish to isolate and use the empty RV-C particles described below as an immunogenic composition.

Method of Producing a Neutralizing Antibody

In another embodiment, the present invention is a method of eliciting neutralizing antibodies against rhinovirus C, the method comprising the steps of providing to a subject an effective amount of an immunogenic composition comprising the immunogen peptide vaccine as described above.

In one version of the invention, one may wish to isolate and use the empty RV-C particles described below as an immunogenic composition.

EXAMPLES

Example 1: Atomic Resolution Structure of Human Rhinovirus C15a, a Virus Linked to Childhood Asthma Exacerbation Results Production of RV-C15a Viruses.

Recently, a recombinant RV-C15 virus[12], adapted for tissue culture growth by serial passage in HeLa-E8 cells[7] (a transduced HeLa cell line expressing CDHR3) led to new protocols for enhanced virus yields. The derivative, RV-C15a, represents a cell-adapted, uncloned population. The consensus sequence of this population differs in the capsid region from that of RV-C15, primarily by a single, high-frequency, nucleotide polymorphism. The substitution converts residue 1125 from Thr to Lys. (Numbering convention adds 1000 to VP1 residues, 2000 to VP2 residues, 3000 to VP3 residues, and 4000 to VP4 residues.) In the present work, an RV-C15a sample, purified only by sucrose cushion sedimentation, was used for cryo-EM structure analysis. To achieve an optimal number of particles per micrograph, data collection was carried out at a low magnification. Specifically, movies of frozen RV-C15a particles within a thin layer of vitreous ice were recorded at a nominal magnification of 14,000× using a Gatan K2 Summit direct electron detector. However, the trade-off was a low signal-to-noise ratio and a high anisotropic magnification distortion compared to what would be the case were high magnifications used for data collection. The primary data were collected in less than one week.

Biochemical Characterization of Two Forms of Particles.

Figure 5:
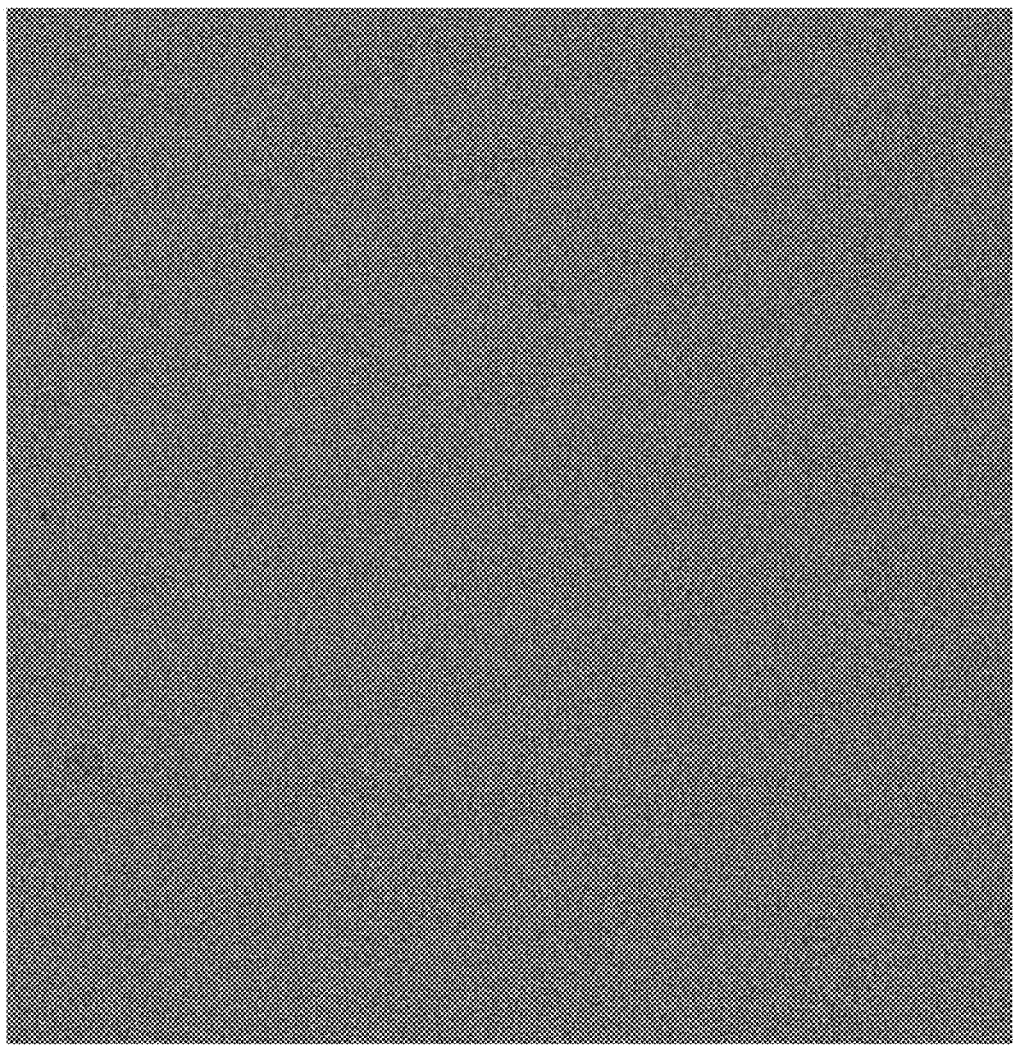
FIG. 5 is an image from a typical cryo electron microscopic micrograph that shows the presence of full and empty RV-C15a particles. This micrograph was recorded at a defocus of 3.1 μm. The scale bar indicates 100 nm.
Figure 7A:
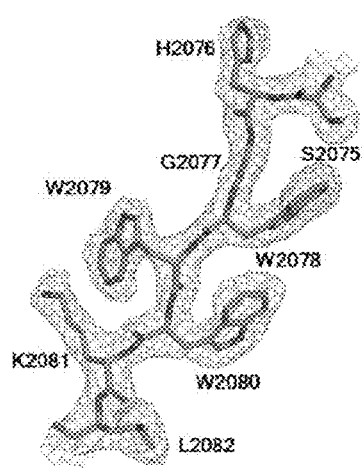
FIG. 7A-7F demonstrates typical densities of the full (A-C) and empty (D-F) particle EM maps.
Figure 7B:
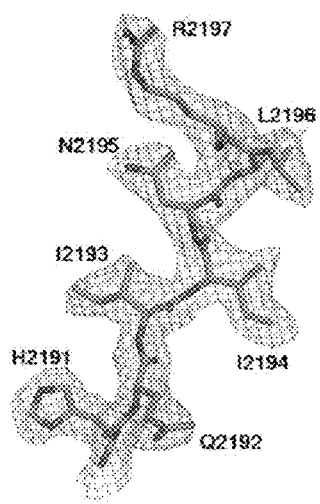
Figure 7C:
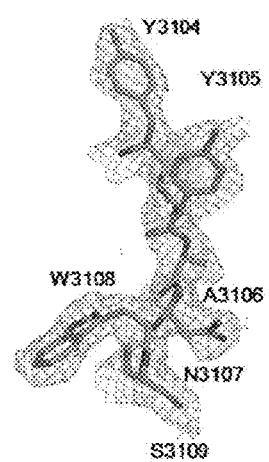
Figure 7D:
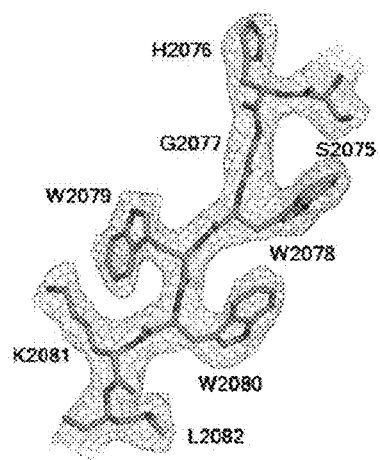
Figure 7E:
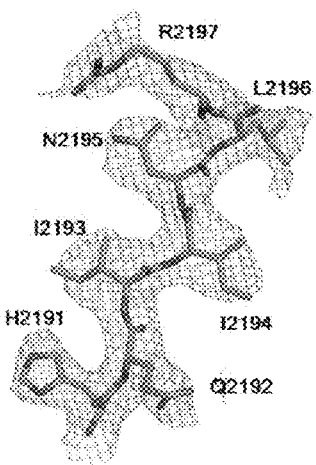
Figure 7F:
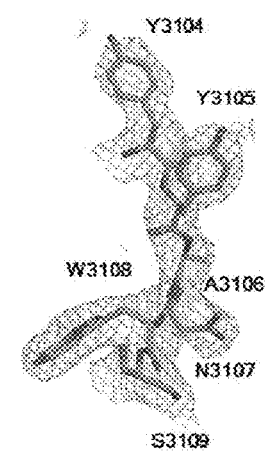

Cryo-EM micrographs of RV-C15a showed the presence of two major forms of particles. One form lacked density at their centers and another form had density at their centers (FIG. 5). When fractionated on sucrose gradients, these types of particles separated from each other. One form was full, infectious virions that contained VP1, VP2, VP3 and VP4 whereas the other form (~30% of all particles) was native empty particles (NEP) that had VP1, VP3, and uncleaved VP0, as shown by western blot analyses using an antibody against VP2 (FIG. 6A). Unlike the full virions, NEPs were devoid of viral RNA and had no infectivity to HeLa-E8 cells (FIG. 6B).

Cryo-EM Structure Determination.

Figure 8A:
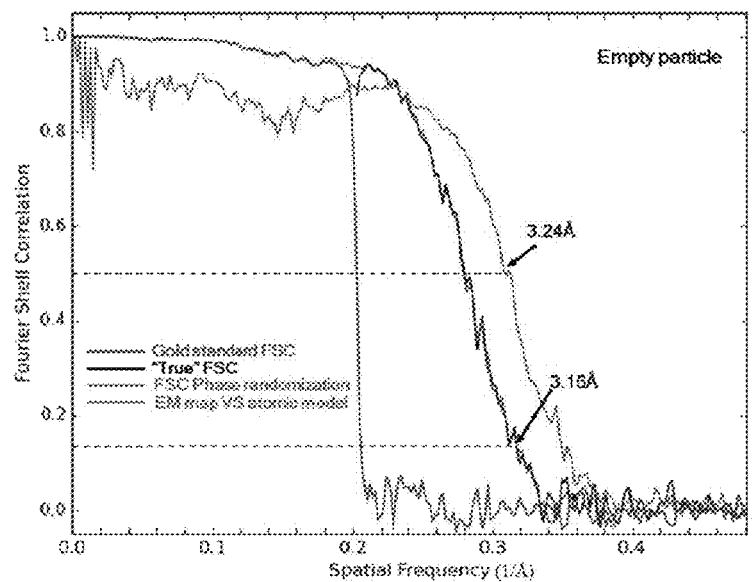
FIGS. 8A-8B shows the resolution of the empty (A) and full (B) particle maps using Fourier Shell Correlation (FSC) curves. The FSC curves between two half subset maps calculated using the original images (Gold standard FSC) and using phase randomized (beyond 5 Å) images (FSC Phase randomization) are colored red and blue. "True" FSC curves are colored black. The FSC curves between the final EM map and a density map computed based on the modeled atomic coordinates were colored green.
Figure 8B:
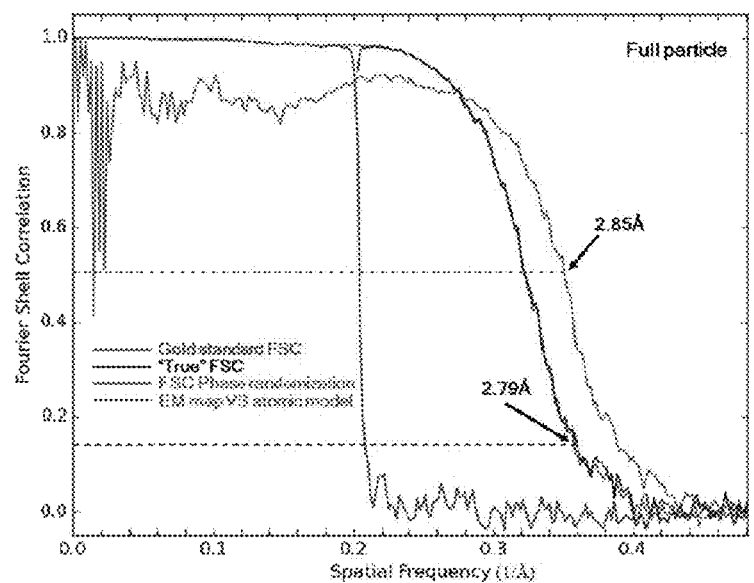

Images of full and empty particles were separated by reference-free 2D classification using the program Relion[16]. A "truly independent" procedure of 3D reconstruction was employed to avoid overfitting to noise[17]. Essentially, initial model calculations, low resolution refinements and high resolution refinements were performed independently for each of the two half-data subsets. Parameters of anisotropic magnification distortion, a major resolution limiting factor for large assemblies (e.g., viruses), were estimated using powder diffraction patterns of polycrystalline gold particles[26]. The resultant parameters were used in the program jspr[17] for correcting anisotropic magnification distortion on individual particles. Refinements of particle center, orientation, defocus, astigmatism, scale, and beam tilt resulted in icosahedral reconstructions of 8,973 full particles and 3,614 empty particles at 2.8 Å and 3.2 Å resolution, respectively (FIG. 7 and Table 2). The resolution of the maps was estimated by calculating the Fourier shell correlation between the two half maps, using 0.143 as a cut-off[27] (FIG. 8).

RV-C15a has a Spiky Structure.

Figure 1B:
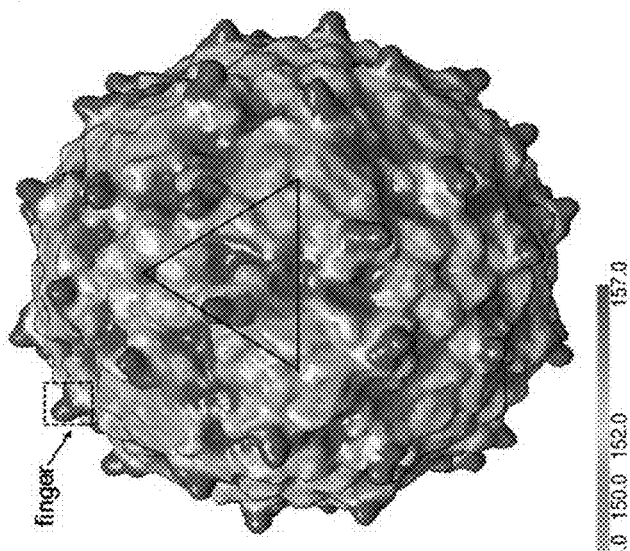
Figure 1C:
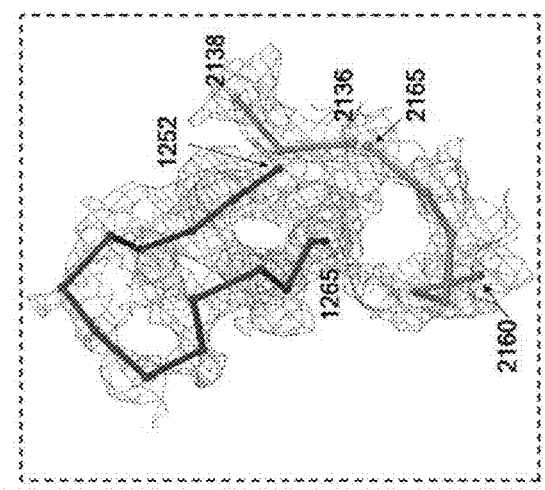
Figure 9A:
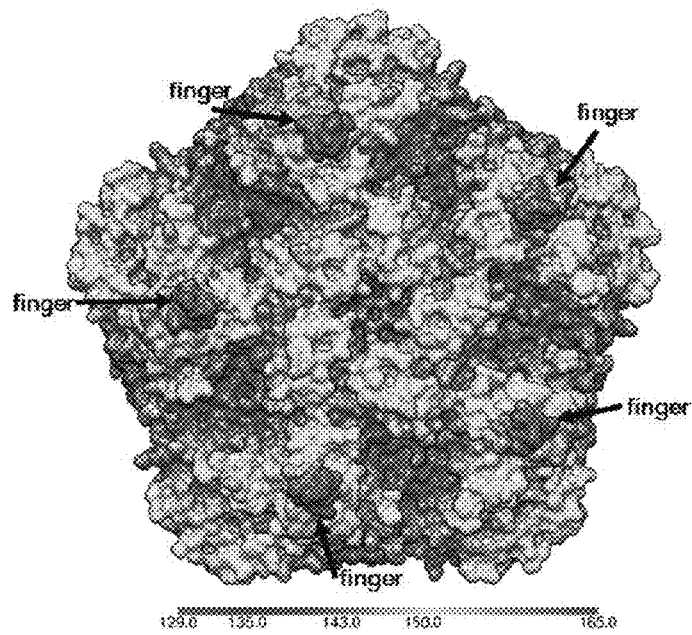
FIG. 9A-9B shows that the finger region on the RV-C15a structure is variable in amino acid sequence among RV-C viruses. A surface representation of a pentamer of the RV-C15a capsid is colored by radial distance (A) to the virus center (A) or by conservation of amino acid sequences (B) among 33 types of RV-C virus. A total of 67 sequences of RV-C viruses for which the complete sequence of P1 region is available are used in sequence alignment. Shown in the color key is the occurrence (%) of the most popular residue at a given alignment position among the 67 sequences.
Figure 9B:
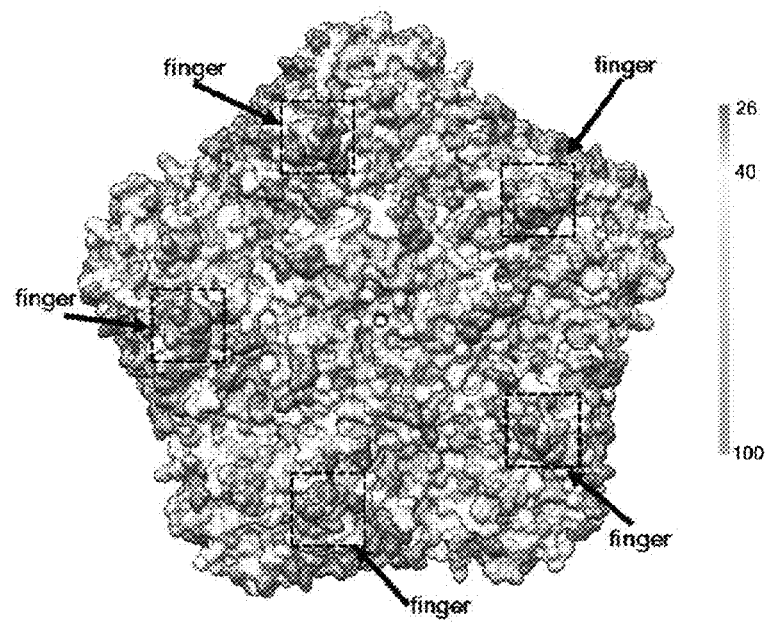

The structure of the RV-C15a full particle has 60 dominant spike-like protrusions, or "fingers," on the outer surface of the virion (FIG. 1). In contrast, all other EV structures have smoother, spherical surfaces (FIG. 1). Each RV-C15a finger, located at the juncture between VP1, VP2 and VP3 that form a protomer, is formed by the VP1 C-terminal residues 1252-1265 as well as residues 2136-2138 and 2160-2165 that form part of the VP2 EF loop (the loop that connects β strand E and β strand F in the jelly roll) (FIG. 1). It is noteworthy that residues 2160-2165 are highly variable among alignments of RV-C sequences[13]. This segment corresponds to the neutralizing immunogenic site NIm-II on the RV-B14 structure[2, 13]. The VP1 contribution to the finger, residues 1252-1265, is an RV-C-specific insertion. This region, is also conserved in length but not in sequence among all members of the RV-C (FIG. 9).

Because of relatively large deletions (21-35 residues) in parts of the VP1 BC, DE and HI loops, the RV-C15a structure lacks a protruding "plateau" around each of the 5-fold vertices, a characteristic feature of other EV (FIG. 1A, B). Thus the RV-C do not have the analogous surface mass near the 5-fold vertices to form immunogenic sites equivalent to NIm-IA (VP1 BC loop) and NIm-IB (VP1 DE loop) on RV-B14[2]. Instead, the finger regions, as mentioned above, probably function as the dominant antigenic sites[13]. As another consequence of these finger regions, the RV-C15a particles have narrow, non-continuous canyons, much like the surface of EV-D68, a virus that also causes respiratory illnesses[5]. In each icosahedral asymmetric unit, the C-proximal, RV-C15a VP1 insertion helps create a wall-like feature blocking the eastern end of the canyon (defined with respect to the usual orientation of picornaviruses used in most figures) (FIG. 1A,B).

A Sequence-Conserved Depression could Bind Glycosylated CDHR3.

Figure 10A:
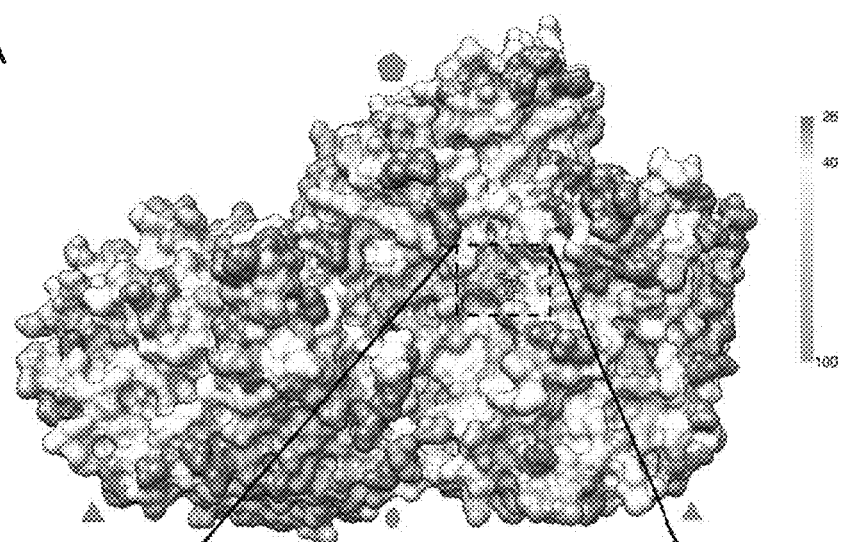
FIGS. 10A-10B show a sequenced-conserved region near the base of the finger on RV-C15a that forms a potential binding site for sialic acid. (A) A surface representation of two protomers of the RV-C15a capsid is colored by conservation of amino acid sequences among 33 types of RV-C virus as in FIG. 9. A black rectangle (dash line) outlines the limit of a close-up view of the potential sialic acid (yellow) binding site shown in (B).
Figure 10B:
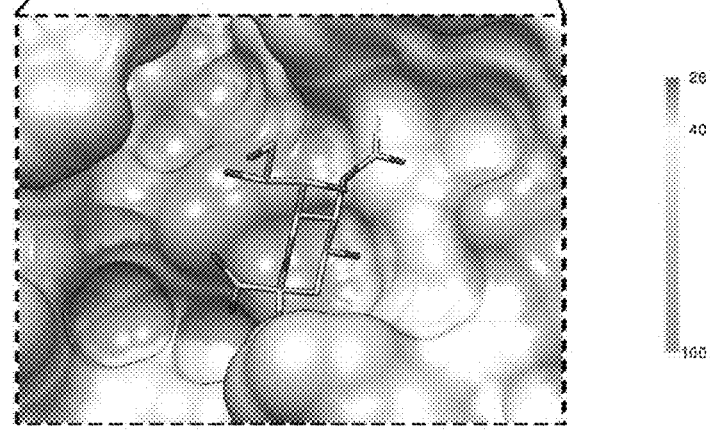

Sialic acid is the glycan moiety recognized by EV-D68 when it interacts with its cellular receptor[24]. Superposition of EV-D68 structure complexed with sialic acid (FIG. 2A) onto the structure of RV-C15a showed that the region near the eastern end of the RV-C15a canyon has a similar surface electrostatic potential as the sialic acid binding site on EV-D68 (FIG. 2B,C). In the EV-D68, sialic acid can be bound mainly by the Pro3231 carbonyl group and by the Arg3104 guanidinium group (FIG. 2D). In RV-C15a, potentially those interactions would be replaced by the structurally equivalent carbonyl group of Pro3226 and by the side chain amino group of Lys1271, respectively (FIG. 2E). Some of the nearby surface residues contributing to this region are conserved among all RV-C (FIG. 10), and it is clear that the overall topography could readily accommodate a sialic acid ligand. Therefore, this region, close to the base of each finger in the RV-C15a structure, is a likely binding site for a CDHR3 glycan. Consistent with this prediction, mutation of Asn186 a key glycosylation site on CDHR3, impairs RV-C15 binding to receptor-expressing cells[7]. Therefore, glycans must play an important role in RV-C receptor interactions, as they do also for EV-D68.

The VP1 Hydrophobic Pocket is Unsuitable for Antiviral Capsid Binding Agents.

Figure 3A:
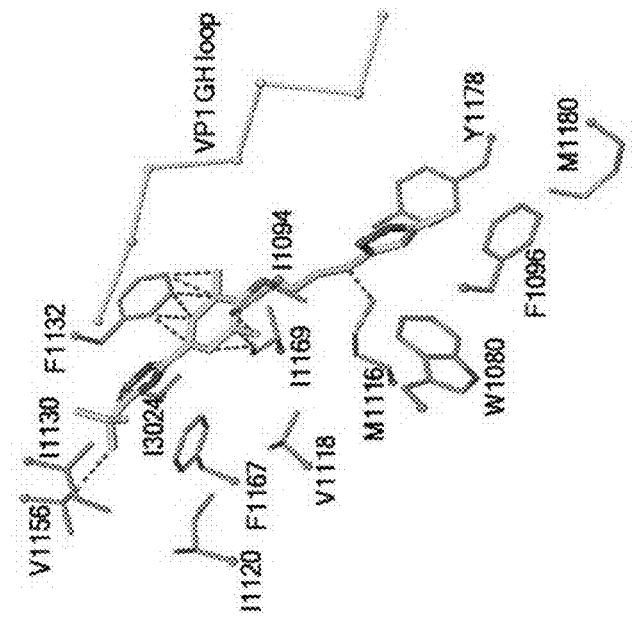
FIGS. 3A-3C shows that RV-C15a has a collapsed VP1 hydrophobic pocket. RV-A16 (A) and RV-C15a (B) are colored according to their polypeptide identity: VP1 (blue), VP2 (green), and VP3 (red). The volume of the VP1 hydrophobic pocket, calculated using Pymol, is colored gold. (C) Residues lining the VP1 pocket of RV-C15a clash with pleconaril (a capsid-binding inhibitor against many EV but not RV-C) when superimposing the structures of RV-C15a and RV-B14 complexed with pleconaril. The VP1 GH loop of RV-B14 (shown in yellow, as c-alpha backbones), adopts a conformation that can accommodate pleconaril. Red dash lines indicate a distance of closer than 2.5 Å between a given atom of a RV-C15 residue (green) and a given atom of pleconaril (yellow). Oxygen, nitrogen and sulfur atoms are colored red, dark blue and dark yellow, respectively.
Figure 3B:
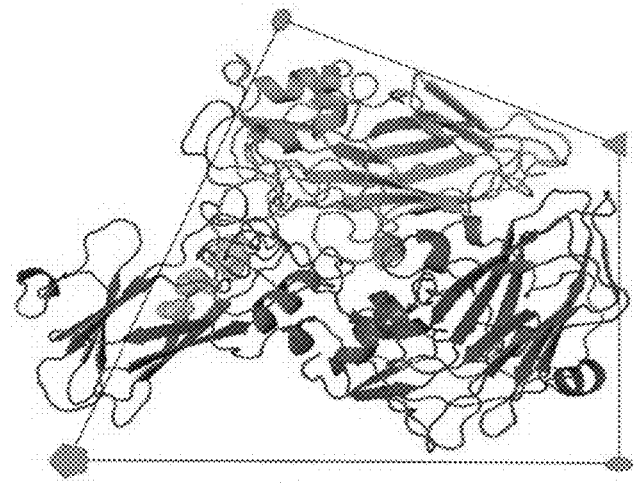
Figure 3C:
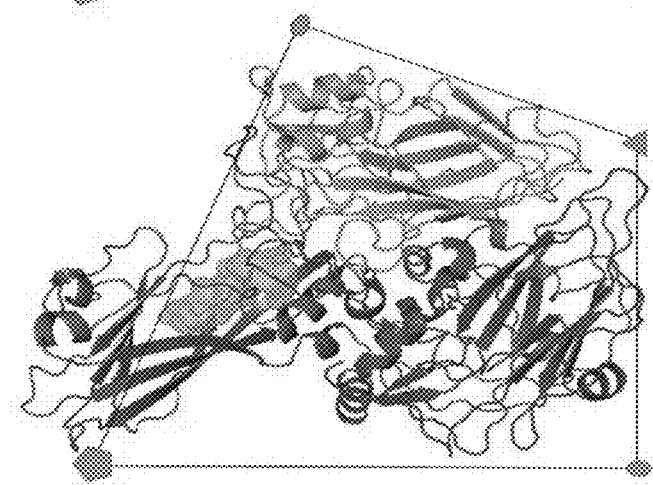

Unlike many EV structures the hydrophobic pocket within the VP1 jelly roll fold, where a pocket factor is typically bound[4, 5, 22], is collapsed in RV-C15a (FIG. 3A, B). The collapsed structure is similar to the empty pockets found in purified RV-B14[2] and RV-B3[28]. None of these three structures have sufficient space to accommodate a fatty-acid pocket factor, because for each, the VP1 GH loop, located at the boundary between the canyon and the entrance to the VP1 pocket, is in a conformation that squeezes the pocket. Nevertheless, in RV-B3 and RV-B14, the flexibility of the VP1 GH loop allows enlargement of the pocket that then can bind antiviral reagents. The RV-B14 pocket is lined with multiple small residues (e.g., Ala, Ser, Val, etc) that can accommodate such compounds. In contrast, the collapsed RV-C15a VP1 pocket is filled with bulky, hydrophobic residues (in particular, Trp1080, Phe1096, Met1116, and Met1180) (FIG. 3C; Table 3). These amino acids are conserved in almost all RV-C[14]. Additionally, Ile1198 and Tyr1246 partially block the entrance to the VP1 pocket. Therefore, as has been observed experimentally[14], no RV-C are likely to be responsive to antiviral therapies based on pocket-binding compounds.

Comparison of the Full and Empty Particle Structures.

Figure 4A:
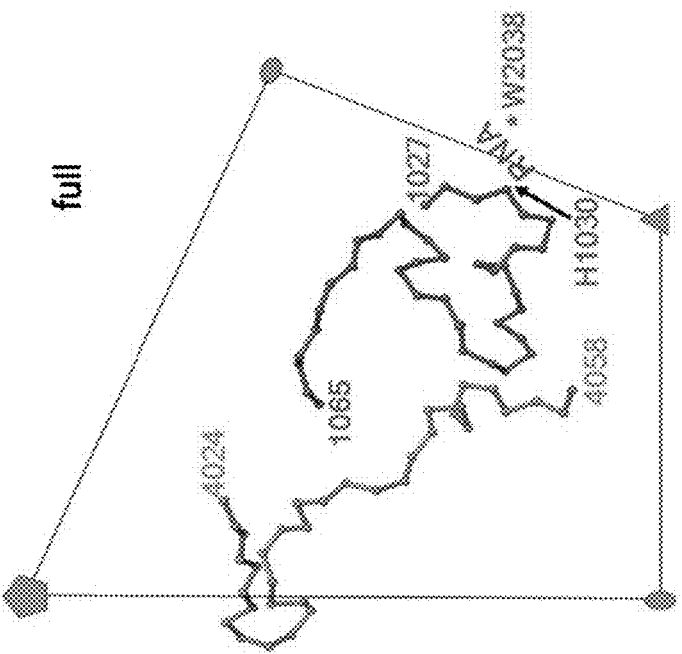
FIGS. 4A-4B demonstrates that the full and empty RV-C15a particle structures differ in regions at the capsid interior. The VP1 N-terminus and VP4 undergo structural rearrangements when the empty particle (A) and full particle (B) structures are compared. Amino acid residues are shown as Cα backbones. VP4, VP2, and VP1 are colored orange, green and blue, respectively. In the RV-C15a full particle structure, His1030, together with a conserved residue Trp2038 shared by many EV, are involved in forming an RNA binding site.
Figure 4B:
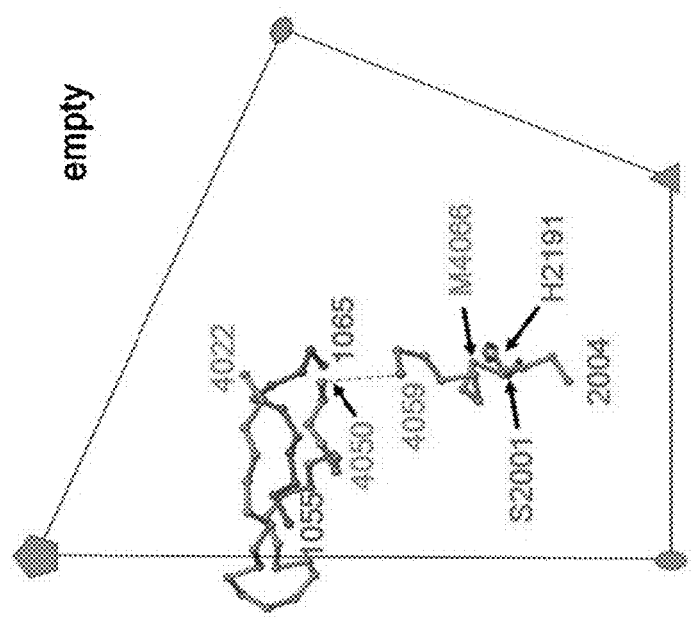

RV-C15a full and empty particles differed mainly in regions on the inner surfaces of their capsid shells (FIG. 4). In particular, the VP1 N-terminal residues 1017-1053 are well-ordered in the full particle map, but disordered in the empty particle map. This is consistent with other EV structures where the VP1 N-terminus is involved in binding to viral RNA[22] and is externalized prior to ejecting the genome during infection[29]. Thus the specific configuration of this internal region is RNA-dependent and is likely to exert strong influence on VP0 cleavage when the RNA is packaged. In the empty particles, VP0 residues 4024-4050 form a hairpin loop positioning the VP0 cleavage site in close proximity to His2191 (FIG. 4A), a crucial residue in the cleavage mechanism[30]. Nearby VP1 residues 1054-1064 interact with the VP0 hairpin within the same protomer, presumably helping to set up the pending cleavage reaction. However, in the full particle structure, the VP1 N-terminal residues 1027-1053, (disordered in the empty particles), interact with the C-terminus of VP4 within the same protomer and participates in viral RNA binding (FIG. 4B).

Discussion

The cryo-EM structure of RV-C15a showed a collapsed hydrophobic pocket in VP1 that is filled with multiple bulky residues that inhibit the entrance of compounds which inhibit other EV by binding into the VP1 pocket. This is reminiscent of the collapsed pockets of non-EV picornaviruses, such as foot-and-mouth disease virus (FMDV, genus Aphthovirus)[31] and Mengovirus (genus Cardiovirus)[32]. Those pockets are similarly occupied by multiple bulky, hydrophobic side chains and are unable to serve as drug targets.

Inclusion of large hydrophobic residues into the VP1 pocket of RV-Cs and incorporation of a fatty-acid like pocket factor into the VP1 pocket of many other EVs produce similar hydrophobic effects that favor the folding of the VP1 "jelly roll" β barrel. On one hand large hydrophobic residues (e.g., Phe, Trp, Met) are more effective than small residues (e.g., Val, Ala) at reducing solvent accessible surface areas in the pocket. Likewise, a pocket factor with a long hydrophobic tail (more than eight carbon atoms) plays a crucial role in expelling water out of the VP1 pocket of many EVs that contain multiple small residues. On the other hand, the presence of large hydrophobic side chains or a pocket factor in a VP1 pocket keeps the two sheets (one with β strands C, H, E, F and the other with β strands B, I, D, G)

in a favorable distance for forming a β barrel and offers hydrophobic interactions that stabilize the "jelly roll" fold.

The large interior rearrangements characterizing the full and the native empty particles of RV-C15a, contrast with the conserved external surfaces. Both particle types have the same diameter, and display the same finger protrusions, truncated 5-fold vertices, and putative glycan binding regions. Possibly the RV-C use these native empty particles as immunogenic molecular decoys during infections, or they are merely byproducts of the assembly process.

The atomic structures of an RV-C virus, as reported here, show novel molecular targets for designing anti-RV-C therapeutics or effective vaccines by utilizing the non-infectious empty particles. These possibilities have clinical relevance since many RV-C, including RV-C15, are associated with severe, hospitalization-category infections in young children, especially those with asthma, and can also lead to significant adult respiratory problems, including chronic obstructive pulmonary disease.

Methods

Growth and Purification of RV-C15a.

RV-C15a (adapted) is a virus preparation derived by serial passage (13×) of recombinant C15 virus[12], in HeLa-E8 cells, a lentivirus-transduced line expressing the full-length human CDHR3 gene (Tyr529) linked to a GFP reporter sequence[7]. To produce viruses for structure determination, HeLa-E8 cells were infected with RV-C15a at 34° C. At 40 h post infection after complete cytopathic effect (CPE) was observed, infected cells (2.4×10$^8$) were supplemented with HEPES (to 50 mM, pH 7.2) and then subject to multiple freeze-thaw cycles (3×). Clarified supernatants were treated with RNAse A, then concentrated by pelleting through 30% sucrose, before resuspension and being assayed for titer[7, 33]. The procedure gave ~1.2×10$^{10}$ PFU/PFUe (by plaque assay/qRT-PCR using HeLa-E8 cells) equivalent to ~125 μg RNA-containing, infectious particles, assuming a particle-to-PFU ratio of ~200.

Characterization of Two Forms of RV-C15a Particles.

A sample of RV-C15a, as prepared for structure determination, was sedimented through a 10-40% sucrose gradient (SW41 rotor, 24,600 rpm for 3 h at 4° C.). Fractions (1 ml) were collected (from the top) and then probed for VP2/VP0 content by Western blot analyses using anti-RV-C15-VP2 mouse monoclonal antibody, clone #517 (kindly provided by MedImmune Inc., Gaithersberg Md.). The fractions were also tested for infectivity according to CPE[34], and for RNA content by qRT-PCR[7].

Cryo-Electron Microscopy.

Aliquots of 2.8 μL of purified RV-C15a sample were applied onto glow-discharged holey carbon EM grids (400 mesh, Ted Pella Inc.). Grids were blotted for ~8 s at a relative humidity of 80% and then plunge-frozen in liquid ethane cooled down by liquid nitrogen using a Cryoplunge 3 system (Gatan). Movies of frozen RV-C15a particles embedded in vitreous ice were collected at liquid nitrogen temperature using a Titan Krios transmission electron microscope (FEI) operated at 300 kV and equipped with a Gatan K2 Summit direct electron detector (3838×3710 in physical pixels). All the movies were automatically recorded in super resolution mode using Leginon[35] at a nominal magnification of 14,000× and with a defocus range of 0.7-3.5 μm. This resulted in a super resolution pixel size of 1.04 Å/pixel. The dose rate was approximately 8e$^-$/pixel/s. For each movie, the total electron dose was about 25.7 e$^-$/Å$^2$ that was fractionated into 70 frames with an exposure time of 200 ms per frame.

Image Processing.

Cryo-EM data were collected of the RV-15a particles. A total of 2979 movies were subjected to whole-frame motion correction using a modified version of MOTIONCORR[15] as modified by Wen Jiang (Purdue University). This process was integrated into the Appion data processing pipeline[36]. Aligned frames were subsequently summed to obtain individual micrographs. Micrographs that had ice contamination or severe drift were discarded. The remaining micrographs were used for estimating of the contrast transfer function (CTF) parameters using CTFFIND3[37]. A total of 24,882 particles were selected initially semi-automatically using e2boxer.py in the EMAN2 package[38] and later automatically using DoG picker[39]. Individual particle images were boxed, extracted and subjected to reference-free 2D classification into 156 classes using the program Relion[16]. Some of these classes were clearly composed of full particles, some of empty particles and some were just junk. This yielded 13,390 full particles and 5,324 empty particles. Particles were re-boxed and re-extracted from the micrographs using jspr[17]. CTF parameters of the particles from each micrograph were estimated using fitctf2.py[40].

Images of the full particles were divided into two half data subsets. A "truly independent" 3D reconstruction strategy, using the program jspr[17], was applied to each of the two subsets assuming icosahedral symmetry. For each subset, eightfold binned particle images (squares of 8×8 original pixels separated by 1.04 Å were averaged to represent one pixel with a spacing of 8.32 Å) were used to compute eight initial 3D reconstructions by assigning random initial angles to each of 150 particle images. Refinements were performed by searching for the best orientation and particle center of each particle image relative to the eight current 3D reconstructions. Three of these structures were selected for further refinement with all the available particle images in the half subset. After multiple iterations these structures converged to roughly the same reconstruction. One of these structures was randomly chosen to extend the refinement with 4-binned, then 2-binned data and finally unbinned data. At this point, anisotropic magnification distortion remained the major resolution limiting factor. Ten images of polycrystalline gold particles were taken at a nominal magnification of 14,000× in super resolution mode. Fourier transform of these gold particle images gave powder diffraction like patterns that were used to estimate parameters of anisotropic magnification distortion[26]. The estimated degree of distortion and angle were 2.87% and 31.3°, respectively. These parameters were then employed to correct anisotropic magnification distortion for individual particle images using jspr[17]. Subsequent refinement of particle center, orientation, defocus, astigmatism, scale and beam tilt using jspr led to the final optimal reconstructions in terms of resolution. Fourier Shell Correlation (FSC) between the two subsets was used to monitor convergence. The same procedures were used for determining the 3D structure of the empty particles. A 2.79 Å resolution map of the full particle was reconstructed using 8,973 particles, and a 3.16 Å resolution map of the empty particle was reconstructed using 3,614 particles. The map resolution was determined based on the FSC between the two half maps (masked with a soft mask) independently calculated using the two half data subsets following the 0.143 cut-off criterion[27, 41]. To further validate the map resolution, phase randomized (beyond 5 Å) data were refined using the same procedures as were used for the original data that were not phase randomized. A "true FSC" curve[42] was calculated using the FSC curve based on the original data and the FSC curve based on the phase randomized data. The full and empty particle maps were sharpened[27] using a B factor of −108.4 Å$^2$ and −122.2 Å$^2$, respectively.

Model Building and Refinement.

For the full particle structure, a predicted atomic structure of the RV-C15[13] (including coordinates for a protomer, VP1-VP4) was manually fitted into a region of the final EM map that corresponds to one protomer of the capsid using Chimera[43]. Atomic positions were refined using Phenix[44] in real space to maximize the correlation coefficient between the final EM map and a map calculated based on the coordinates. Model statistics including bond lengths, bond angles and all-atom clash, rotamer statistics, and Ramachandran plot statistics were monitored. This was followed by model rebuilding with the program Coot[45]. The combination of real space refinement in Phenix and model rebuilding in Coot were repeated multiple times to achieve an optimized fit between the coordinates and the final EM map. At this point, the coordinates fit well into the densities by visual inspection.

Next, a mask, which included all grid points within a radius of 5 Å around each atom, was employed to cut out densities from the final EM map using the CCP4[46] program suite. The resultant segment of the final EM map was placed into a pseudo crystallographic unit cell (P1 space group) and was back transformed into pseudo structure factors (including both amplitudes and phases.) The coordinates were then subjected to refinement of individual B factors, atom positions and occupancy against the pseudo structure factors using standard reciprocal space refinement procedures in Phenix[44]. R factors were monitored during the refinement cycles. Only the coordinates were refined, whereas the map was kept constant. Subsequently, the coordinates were refined in real space against the final EM map by applying non-crystallographic symmetry (60-fold) constraints using Phenix[44]. Validation of the final coordinates was based on the criteria of MolProbity[47]. The full particle atomic model (excluding VP4 and the VP1 N-terminal residues 1101-1160) was used as a starting atomic model for model building and refinement of the empty particle structure.

As a further validation of the EM map resolution and of the fitting between the atomic model and the final EM map, a density map was calculated based on the atomic model specifying a resolution of 2.79 Å for the full particle structure and 3.16 Å for the empty particle structure. An FSC was computed between the resultant density map and the final EM map. The resolution determined using 0.5 FSC as a cut-off was 2.85 Å (full particle) and 3.24 Å (empty particle). Oligomers were generated using VIPERdb[48]. Figures were made using Chimera[43] and Pymol (www.pymol.org).

Example 2—Identification of an RV-C15 Immunogenic Site

Example 2 refers to FIGS. 11-14. This set of experiments is drawn to an understanding of the dominant RV-C15 epitope.

Referring to FIG. 11, the atomic resolution structure of rhinovirus C15a shows 1 of 60 icosametric protein subunits, each composed of 4 viral proteins, VP1 (blue), VP2 (green), VP3 (red) and VP4 (yellow). The peptide sequences identified from this structure with putative immunogenic potential (VP1 and VP2) are highlighted. PDB coordinates for this structure have been submitted for publication (Yue et al, 2016).

Peptide sequences chosen for peptide antibody analysis in the RVC15a VP1 and VP2 proteins are highlighted in FIG. 12.

Figure 13:
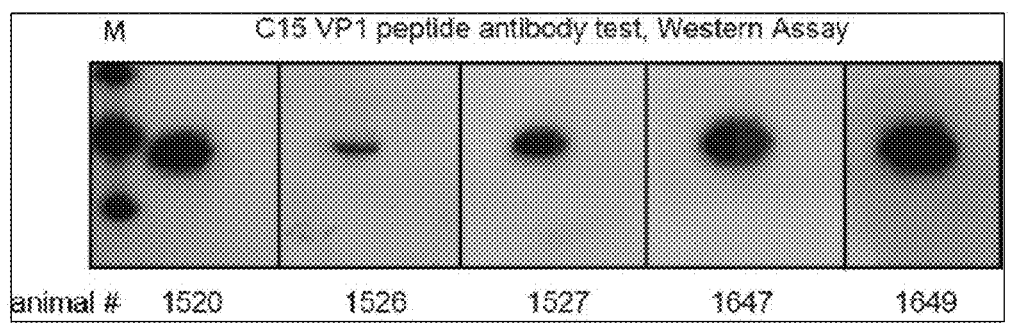
FIG. 13 is a Western analysis of C15 VP1 peptide antibodies.
Figure 14:
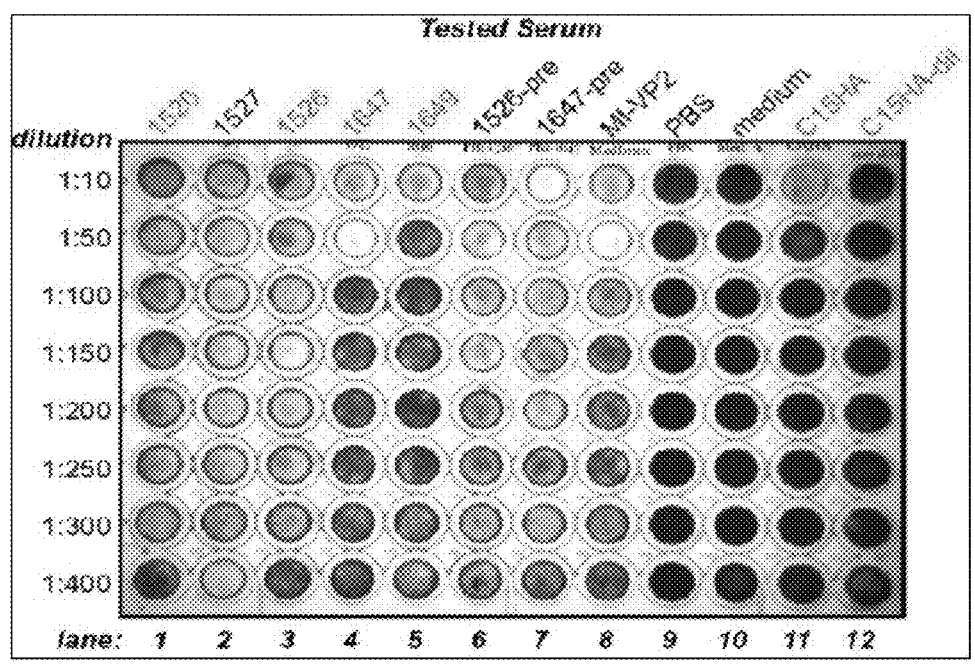
FIG. 14 is a microneutralization assay.

Referring to FIG. 13, a Western analysis shows that the sera of inoculated experimental animals react to the peptides disclosed in FIG. 12. Five mice each were inoculated with the VP1 or VP2 peptides disclosed in FIG. 12. Serum bleeds were tested in Western analyses with proteins from C15a virus. None of the VP2-receiving animals had a positive response (not shown), but all 5 of the VP1-receiving animals had sera reacting with the viral VP1 protein. GenScript USA Inc, 860 Centennial Ave, Piscataway, N.J., 08854. Order ID: 549712-13 and 54712-18.

FIG. 14 shows a microneutralization assay. Aliquots of C15a virus were incubated with the indicated dilutions of the above VP1 peptide sera, on the 96 well plates (1 hr 34° C.). HeLa cells were added to each well. After 72 hrs (34° C.), the surviving cells were stained for viability. The "darker" the well, the more surviving (Ab-protected) cells. Lanes 6-12 are control samples. Lanes 1-5 are the VP1 sera from FIG. 13.

Our conclusion is that serum from animals: 1520, 1526, 1647 and 1649 (shown in red in FIG. 14) show cell protection against virus infection/lysis and must contain at least some viable concentration of neutralizing antibodies. Therefore, the VP1 peptide used to inoculate these mice contains a protective NIM (neutralizing immunogenic) epitope.

TABLE 2

Cryo-EM data statistics.

| | RV-C15a full particle | RV-C15a empty particle |
|---|---|---|
| EM data collection and processing | | |
| Microscope | Titan Krios | Titan Krios |
| Accelerating voltage (kV) | 300 | 300 |
| Camera | Gatan K2 Summit | Gatan K2 Summit |
| Pixel size[a] (Å/pixel) | 1.04 | 1.04 |
| Dose rate ($e^-$/pixel/s) | 8 | 8 |
| Total dose ($e^-$/Å$^2$) | 25.7 | 25.7 |
| Number of particles for the final reconstruction | 8973 | 3614 |
| Resolution[b] (Å) | 2.79 | 3.16 |
| Map sharpening B factor (Å$^2$) | −108.4 | −122.2 |
| Model Statistics | | |
| Correlation coefficient (around atoms)[c] | 0.883 | 0.880 |
| Number of atoms | | |
| Protein | 6221 | 6007 |
| Water | 60 | 0 |
| Avg. B-factor (Å$^2$) | 24.1 | 31.7 |
| r.m.s deviations[d] | | |
| Bond lengths (Å) | 0.010 | 0.010 |
| Bond angles (°) | 1.073 | 0.944 |
| Ramachadran plot[d] | | |
| Favored (%) | 93.5 | 92.0 |
| Allowed (%) | 6.4 | 7.6 |
| Outliers (%) | 0.1 | 0.4 |

[a]Pixel size in super resolution mode. The physical pixel size is 2.08 Å/pixel.
[b]Resolution was determined by the Fourier shell correlation between two half-maps using 0.143 as a cut-off value.
[c]Real space correlation coefficient (around atoms) between the final EM map and a density map calculated based on the coordinates.
[d]Based on the criteria of Molprobity (44)

TABLE 3

Comparison of amino acid residues lining the VP1 hydrophobic pocket among enteroviruses[a].

| Residues[b] | RV-C15a | RV-A16 (1AYM) | RV-B14 (4RHV) | EV-A71 (3ZFE) | CVB3 (1COV) | PV1 (1ASJ) | EV-D68 (4WM8) |
|---|---|---|---|---|---|---|---|
| 1096 | Phe | Leu | Leu | Ile | Pro | Tyr | Thr |
| 1106 | Phe | Phe | Leu | Val | Leu | Leu | Leu |
| 1114 | Phe | Phe | Phe | Phe | Phe | Phe | Phe |
| 1178 | Tyr | Tyr | Tyr | Tyr | Tyr | Tyr | Tyr |
| 1180 | Met | Met | Cys | Trp | Asn | His | Val |
| 1198 | Ile | Thr | Ile | Ala | Ile | Ala | Ile |
| 1246 | Tyr | His | Gly | Ala | Lys | — | Ala |
| 1080 | Trp | Ile | Val | Val | Val | Val | Val |
| 1092 | Trp | Trp | Trp | Trp | Trp | Trp | Trp |
| 1094 | Ile | Ile | Ile | Ile | Ile | Ile | Ile |
| 1116 | Met | Ser | Ser | Ala | Leu | Met | Ala |
| 1169 | Ile | Leu | Val | Val | Val | Val | Ile |
| 1204 | Met | Met | Met | Met | Met | Phe | Ile |
| 1224 | Val | His | His | Met | Phe | Leu | Met |
| *1118* | *Val* | *Ile* | *Tyr* | *Phe* | *Leu* | *Leu* | *Ile* |
| *1120* | *Ile* | *Met* | *Ile* | *Phe* | *Phe* | *Phe* | *Ile* |
| *1130* | *Ile* | *Tyr* | *Ala* | *Tyr* | *Ile* | *Ile* | *Ala* |
| *1132* | *Phe* | *Tyr* | *Tyr* | *Phe* | *Tyr* | *Tyr* | *Phe* |
| *1154* | *Pro* | *Ala* | *Pro* | *Pro* | *Pro* | *Pro* | *Ala* |
| *1156* | *Val* | *Val* | *Val* | *Val* | *Val* | *Ile* | *Val* |
| *1167* | *Phe* | *Phe* | *Phe* | *Val* | *Met* | *Ile* | *Met* |
| *1207* | *Leu* | *Leu* | *Met* | *Phe* | *Leu* | *Leu* | *Leu* |
| *3024* | *Ile* | *Ala* | *Ala* | *Ile* | *Ala* | *Ala* | *Val* |

[a]In analogy with EV that have a pocket factor bound in the VP1 pocket, RV-C15a residues that are close to the head, the middle part, and the end of the pocket factor are colored bold, white, and italics, respectively.
[b]Residues are numbered based on RV-C15a numbering.

REFERENCES

1. Knowles N J, et al. Picornaviridae. In: *Virus Taxonomy: Classification and Nomenclature of Viruses: Ninth Report of the International Committee on Taxonomy of Viruses* (eds King A M Q, Adams M J, Carstens E B, Lefkowitz E J). Elsevier (2012).
2. Rossmann M G, et al. Structure of a human common cold virus and functional relationship to other picornaviruses. *Nature* 317, 145-153 (1985).
3. Hogle J M, Chow M, Filman D J. Three-dimensional structure of poliovirus at 2.9 Å resolution. *Science* 229, 1358-1365 (1985).
4. Hogle J M. A 3D framework for understanding enterovirus 71. *Nat. Struct. Mol. Biol.* 19, 367-368 (2012).
5. Liu Y, et al. Structure and inhibition of EV-D68, a virus that causes respiratory illness in children. *Science* 347, 71-74 (2015).
6. Miller E K, et al. Human rhinovirus C associated with wheezing in hospitalised children in the Middle East. *J. Clin. Virol.* 46, 85-89 (2009).
7. Bochkov Y A, et al. Cadherin-related family member 3, a childhood asthma susceptibility gene product, mediates rhinovirus C binding and replication. *Proc. Natl. Acad. Sci. U.S.A.* 112, 5485-5490 (2015).
8. Drysdale S B, et al. Respiratory outcome of prematurely born infants following human rhinovirus A and C infections. *Eur. J. Pediatr.* 173, 913-919 (2014).
9. Piralla A, et al. Clinical severity and molecular typing of human rhinovirus C strains during a fall outbreak affecting hospitalized patients. *J. Clin. Virol.* 45, 311-317 (2009).
10. Bizzintino J, et al. Association between human rhinovirus C and severity of acute asthma in children. *Eur. J. Pediatr.* 37, 1037-1042 (2011).
11. Arden K E, McErlean P, Nissen M D, Sloots T P, Mackay I M. Frequent detection of human rhinoviruses, paramyxoviruses, coronaviruses, and bocavirus during acute respiratory tract infections. *J. Med. Virol.* 78, 1232-1240 (2006).
12. Bochkov Y A, et al. Molecular modeling, organ culture and reverse genetics for a newly identified human rhinovirus C. *Nature Med.* 17, 627-632 (2011).
13. Basta H A, Sgro J Y, Palmenberg A C. Modeling of the human rhinovirus C capsid suggests a novel topography with insights on receptor preference and immunogenicity. *Virology* 448, 176-184 (2014).
14. Basta H A, Ashraf S, Sgro J Y, Bochkov Y A, Gem J E, Palmenberg A C. Modeling of the human rhinovirus C capsid suggests possible causes for antiviral drug resistance. *Virology* 448, 82-90 (2014).
15. Li X, et al. Electron counting and beam-induced motion correction enable near-atomic-resolution single-particle cryo-EM. *Nat. Methods* 10, 584-590 (2013).
16. Scheres S H. RELION: implementation of a Bayesian approach to cryo-EM structure determination. *J. Struct. Biol.* 180, 519-530 (2012).
17. Guo F, Jiang W. Single particle cryo-electron microscopy and 3-D reconstruction of viruses. *Methods Mol. Biol.* 1117, 401-443 (2014).
18. Bartesaghi A, et al. 2.2 Å resolution cryo-EM structure of beta-galactosidase in complex with a cell-permeant inhibitor. *Science* 348, 1147-1151 (2015).
19. Basavappa R, Syed R, Flore O, Icenogle J P, Filman D J, Hogle J M. Role and mechanism of the maturation cleavage of VP0 in poliovirus assembly: structure of the empty capsid assembly intermediate at 2.9 Å resolution. *Protein Sci.* 3, 1651-1669 (1994).
20. Rossmann M G, He Y, Kuhn R J. Picornavirus-receptor interactions. *Trends Microbiol.* 10, 324-331 (2002).
21. Rossmann M G. The canyon hypothesis. Hiding the host cell receptor attachment site on a viral surface from immune surveillance. *J. Biol. Chem.* 264, 14587-14590 (1989).

22. Filman D J, Syed R, Chow M, Macadam A J, Minor P D, Hogle J M. Structural factors that control conformational transitions and serotype specificity in type 3 poliovirus. *EMBO J.* 8, 1567-1579 (1989).
23. Smyth M, Pettitt T, Symonds A, Martin J. Identification of the pocket factors in a picornavirus. *Arch. Virol.* 148, 1225-1233 (2003).
24. Liu Y, et al. Sialic acid-dependent cell entry of human enterovirus D68. *Nat. Commun.* 6, 8865 (2015).
25. Rogers J M, Diana G D, McKinlay M A. Pleconaril. A broad spectrum antipicornaviral agent. *Adv. Exp. Med. Biol.* 458, 69-76 (1999).
26. Grant T, Grigorieff N. Automatic estimation and correction of anisotropic magnification distortion in electron microscopes. *J. Struct. Biol.* 192, 204-208 (2015).
27. Rosenthal P B, Henderson R. Optimal determination of particle orientation, absolute hand, and contrast loss in single-particle electron cryomicroscopy. *J. Mol. Biol.* 333, 721-745 (2003).
28. Zhao R, et al. Human rhinovirus 3 at 3.0 Å resolution. *Structure* 4, 1205-1220 (1996).
29. Fricks C E, Hogle J M. Cell-induced conformational change in poliovirus: externalization of the amino terminus of VP1 is responsible for liposome binding. *J. Virol.* 64, 1934-1945 (1990).
30. Hindiyeh M, Li Q H, Basavappa R, Hogle J M, Chow M. Poliovirus mutants at histidine 195 of VP2 do not cleave VP0 into VP2 and VP4. *J. Virol.* 73, 9072-9079 (1999).
31. Acharya R, Fry E, Stuart D, Fox G, Rowlands D, Brown F. The three-dimensional structure of foot-and-mouth disease virus at 2.9 A resolution. *Nature* 337, 709-716 (1989).
32. Luo M, et al. The atomic structure of Mengo virus at 3.0 A resolution. *Science* 235, 182-191 (1987).
33. Griggs T F, Bochkov Y A, Nakagome K, Palmenberg A C, Gem J E. Production, purification, and capsid stability of rhinovirus C types. *J. Virol. Methods* 217, 18-23 (2015).
34. Ledford R M, Collett M S, Pevear D C. Insights into the genetic basis for natural phenotypic resistance of human rhinoviruses to pleconaril. *Antiviral Res.* 68, 135-138 (2005).
35. Suloway C, et al. Automated molecular microscopy: the new Leginon system. *J. Struct. Biol.* 151, 41-60 (2005).
36. Lander G C, et al. Appion: an integrated, database-driven pipeline to facilitate EM image processing. *J. Struct. Biol.* 166, 95-102 (2009).
37. Mindell J A, Grigorieff N. Accurate determination of local defocus and specimen tilt in electron microscopy. *J. Struct. Biol.* 142, 334-347 (2003).
38. Tang G, et al. EMAN2: an extensible image processing suite for electron microscopy. *J. Struct. Biol.* 157, 38-46 (2007).
39. Voss N R, Yoshioka C K, Radermacher M, Potter C S, Carragher B. DoG Picker and TiltPicker: software tools to facilitate particle selection in single particle electron microscopy. *J. Struct. Biol.* 166, 205-213 (2009).
40. Jiang W, Guo F, Liu Z. A graph theory method for determination of cryo-EM image focuses. *J. Struct. Biol.* 180, 343-351 (2012).
41. Scheres S H, Chen S. Prevention of overfitting in cryo-EM structure determination. *Nat. Methods* 9, 853-854 (2012).
42. Chen S, et al. High-resolution noise substitution to measure overfitting and validate resolution in 3D structure determination by single particle electron cryomicroscopy. *Ultramicroscopy* 135, 24-35 (2013).
43. Pettersen E F, et al. UCSF Chimera—a visualization system for exploratory research and analysis. *J. Comput. Chem.* 25, 1605-1612 (2004).
44. Adams P D, et al. PHENIX: a comprehensive Python-based system for macromolecular structure solution. *Acta Crystallogr. D Biol. Crystallogr.* 66, 213-221 (2010).
45. Emsley P, Lohkamp B, Scott W G, Cowtan K. Features and development of Coot. *Acta Crystallogr. D Biol. Crystallogr.* 66, 486-501 (2010).
46. Collaborative Computational Project No. 4. The CCP4 suite: programs for protein crystallography. *Acta Crystallogr. D Biol. Crystallogr.* 50, 760-763 (1994).
47. Chen V B, et al. MolProbity: all-atom structure validation for macromolecular crystallography. *Acta Crystallogr. D Biol. Crystallogr.* 66, 12-21 (2010).
48. Carrillo-Tripp M, et al. VIPERdb2: an enhanced and web API enabled relational database for structural virology. *Nucleic Acids Res.* 37, D436-442 (2009).

We claim:

1. A composition comprising a peptide of the rhinovirus structural protein 1 (VP1) of rhinovirus C and a heterologous carrier protein, wherein the peptide consisting of an amino acid sequence selected from the group consisting of SEQ ID NO:1, 3, 6, 8, 11, 13, 15, 17, 19, 21, 23, 25, 27, 30, 33, 36, 38, 40, 42, 44, 46, 48, 50, 52, 54, 57, 59, 61, 63, 65, 67, 48, 71, 73, 75, 78, 80, 82, 84, 86, 88, 90, 92, 94, 96, 98, 100, 102, 104, 106, 108, 110, 112, 114, 117, 119, 121, 123, 125, and 127.

2. The composition of claim 1, wherein the peptide is bound to the carrier protein.

3. The composition of claim 1, wherein the peptide comprises SEQ ID NO: 1 (YKPNSSGPDEHVLKD).

4. A vaccine comprising a rhinovirus immunogen peptide consisting of an amino acid sequence selected from the group consisting of SEQ ID NO:1, 3, 6, 8, 11, 13, 15, 17, 19, 21, 23, 25, 27, 30, 33, 36, 38, 40, 42, 44, 46, 48, 50, 52, 54, 57, 59, 61, 63, 65, 67, 48, 71, 73, 75, 78, 80, 82, 84, 86, 88, 90, 92, 94, 96, 98, 100, 102, 104, 106, 108, 110, 112, 114, 117, 119, 121, 123, 125, and 127, and an adjuvant or heterologous carrier protein.

5. A pharmaceutical composition comprising the vaccine of claim 4.

6. An expression vector comprising a polynucleotide operably linked to a heterologous transcriptional regulatory element wherein the polynucleotide encodes an immunogen peptide consisting of an amino acid sequence selected from the group consisting of SEQ ID NO:1, 3, 6, 8, 11, 13, 15, 17, 19, 21, 23, 25, 27, 30, 33, 36, 38, 40, 42, 44, 46, 48, 50, 52, 54, 57, 59, 61, 63, 65, 67, 48, 71, 73, 75, 78, 80, 82, 84, 86, 88, 90, 92, 94, 96, 98, 100, 102, 104, 106, 108, 110, 112, 114, 117, 119, 121, 123, 125, and 127.

7. The expression vector of claim 6, wherein the immunogen peptide is SEQ ID NO: 1 (YKPNSSGPDEHVLKD).

8. An isolated cell comprising the expression vector of claim 6.

9. The isolated cell of claim 8, wherein the cell expresses the peptide.

10. The peptide expressed by the isolated cell of claim 9.

11. A method of eliciting an immune response against rhinovirus in a subject, the method comprising administering by injection to the subject a composition of claim 1.

12. A method for immunizing a subject against rhinovirus infection, which comprises administering by injection to a subject an effective amount of the pharmaceutical composition of claim 5.

13. The method of claim 12, wherein the rhinovirus infection is a human rhinovirus C virus.

14. The method of claim 12, wherein the vaccine comprises the peptide coupled to a carrier molecule.

15. A method of eliciting neutralizing antibodies against rhinovirus C, the method comprising the steps of injecting into a subject an effective amount of the composition of claim 1.

* * * * *

UNITED STATES PATENT AND TRADEMARK OFFICE
CERTIFICATE OF CORRECTION

PATENT NO. : 10,428,116 B2
APPLICATION NO. : 15/491513
DATED : October 1, 2019
INVENTOR(S) : Ann C. Palmenberg et al.

Page 1 of 1

It is certified that error appears in the above-identified patent and that said Letters Patent is hereby corrected as shown below:

In the Specification

Column 2, Line 31, "(A)" should be --(Å)--.

Column 3, Line 31, "(A)" should be --(Å)--.

Column 21, Line 36, "Gem" should be --Gern--.

Signed and Sealed this
Nineteenth Day of November, 2019

Andrei Iancu
*Director of the United States Patent and Trademark Office*

SEQUENCE LISTING

```
<160> NUMBER OF SEQ ID NOS: 130

<210> SEQ ID NO 1
<211> LENGTH: 15
<212> TYPE: PRT
<213> ORGANISM: Rhinovirus C15a

<400> SEQUENCE: 1

Tyr Lys Pro Asn Ser Ser Gly Pro Asp Glu His Val Leu Lys Asp
1               5                   10                  15

<210> SEQ ID NO 2
<211> LENGTH: 4
<212> TYPE: PRT
<213> ORGANISM: Rhinovirus C

<400> SEQUENCE: 2

Thr Asn Tyr Asn
1
```

```
<210> SEQ ID NO 3
<211> LENGTH: 12
<212> TYPE: PRT
<213> ORGANISM: Rhinovirus C1

<400> SEQUENCE: 3

Lys Gln Lys Pro Asp Ser Gly Gly Gln Val Glu Pro
1               5                   10

<210> SEQ ID NO 4
<211> LENGTH: 13
<212> TYPE: PRT
<213> ORGANISM: Rhinovirus C1

<400> SEQUENCE: 4

Lys His Phe Leu Asn Thr Arg Asn Asp Ile Lys Asn Leu
1               5                   10

<210> SEQ ID NO 5
<211> LENGTH: 4
<212> TYPE: PRT
<213> ORGANISM: Rhinovirus C

<400> SEQUENCE: 5

Pro Asn Tyr His
1

<210> SEQ ID NO 6
<211> LENGTH: 11
<212> TYPE: PRT
<213> ORGANISM: Rhinovirus C2

<400> SEQUENCE: 6

Thr Asn Lys Gly Ser Thr Thr Glu Leu Glu Glu
1               5                   10

<210> SEQ ID NO 7
<211> LENGTH: 13
<212> TYPE: PRT
<213> ORGANISM: Rhinovirus C2

<400> SEQUENCE: 7

Lys His Tyr Ile Asn Thr Arg Thr Thr Ile Lys Thr Ala
1               5                   10

<210> SEQ ID NO 8
<211> LENGTH: 12
<212> TYPE: PRT
<213> ORGANISM: Rhinovirus C3

<400> SEQUENCE: 8

Lys Pro Lys Thr Ser Gly Ser Thr Glu Leu Glu Pro
1               5                   10

<210> SEQ ID NO 9
<211> LENGTH: 13
<212> TYPE: PRT
<213> ORGANISM: Rhinovirus C3

<400> SEQUENCE: 9

Lys His Phe Phe Lys Tyr Arg Gln Asp Ile Thr Ser Ile
1               5                   10
```

```
<210> SEQ ID NO 10
<211> LENGTH: 4
<212> TYPE: PRT
<213> ORGANISM: Rhinovirus C

<400> SEQUENCE: 10

Thr Asn Tyr His
1

<210> SEQ ID NO 11
<211> LENGTH: 13
<212> TYPE: PRT
<213> ORGANISM: Rhinovirus C4

<400> SEQUENCE: 11

Val Lys Lys Pro Asp Asp Thr Thr Gly Leu Leu Ile Gln
1               5                   10

<210> SEQ ID NO 12
<211> LENGTH: 13
<212> TYPE: PRT
<213> ORGANISM: Rhinovirus C4

<400> SEQUENCE: 12

Lys His Phe Ile Asn His Arg Thr Asp Ile Lys Thr Ala
1               5                   10

<210> SEQ ID NO 13
<211> LENGTH: 14
<212> TYPE: PRT
<213> ORGANISM: Rhinovirus C5

<400> SEQUENCE: 13

Arg Arg Val Asn Pro Asn Ser Glu Asp Ser Thr Leu Thr Arg
1               5                   10

<210> SEQ ID NO 14
<211> LENGTH: 13
<212> TYPE: PRT
<213> ORGANISM: Rhinovirus C5

<400> SEQUENCE: 14

Asp His Tyr Ile Lys Thr Arg Ala Thr Val Thr Thr Ala
1               5                   10

<210> SEQ ID NO 15
<211> LENGTH: 12
<212> TYPE: PRT
<213> ORGANISM: Rhinovirus C6

<400> SEQUENCE: 15

Lys Pro Lys Thr Lys Gly Ser Asn Glu Leu Glu Pro
1               5                   10

<210> SEQ ID NO 16
<211> LENGTH: 13
<212> TYPE: PRT
<213> ORGANISM: Rhinovirus C6

<400> SEQUENCE: 16

Lys His Phe Leu Lys Tyr Arg Asp Asp Ile Thr Ser Ile
1               5                   10
```

```
<210> SEQ ID NO 17
<211> LENGTH: 12
<212> TYPE: PRT
<213> ORGANISM: Rhinovirus C7

<400> SEQUENCE: 17

Val Ile Lys Lys Gly Thr Thr Ser Asp Leu Glu Gln
1               5                   10

<210> SEQ ID NO 18
<211> LENGTH: 13
<212> TYPE: PRT
<213> ORGANISM: Rhinovirus C7

<400> SEQUENCE: 18

Lys His Phe Leu Thr Tyr Arg Thr Asp Ile Thr Asn Val
1               5                   10

<210> SEQ ID NO 19
<211> LENGTH: 13
<212> TYPE: PRT
<213> ORGANISM: Rhinovirus C8

<400> SEQUENCE: 19

Tyr Lys Ala Pro Asp Ala Thr Pro Gln Gln Leu Glu Ser
1               5                   10

<210> SEQ ID NO 20
<211> LENGTH: 13
<212> TYPE: PRT
<213> ORGANISM: Rhinovirus C8

<400> SEQUENCE: 20

Arg His Phe Met Lys Phe Arg Glu Gln Ile Lys Asn Val
1               5                   10

<210> SEQ ID NO 21
<211> LENGTH: 12
<212> TYPE: PRT
<213> ORGANISM: Rhinovirus C9

<400> SEQUENCE: 21

Thr Pro Thr Gly Ala Ser Asp Gly Thr Leu Lys Glu
1               5                   10

<210> SEQ ID NO 22
<211> LENGTH: 13
<212> TYPE: PRT
<213> ORGANISM: Rhinovirus C9

<400> SEQUENCE: 22

Lys His Tyr Leu Lys His Arg Asp Asp Ile Lys Asn Leu
1               5                   10

<210> SEQ ID NO 23
<211> LENGTH: 12
<212> TYPE: PRT
<213> ORGANISM: Rhinovirus C10

<400> SEQUENCE: 23

Lys Pro Glu Thr Glu Gly Ser Asn Ile Leu Ile Gln
1               5                   10
```

```
<210> SEQ ID NO 24
<211> LENGTH: 13
<212> TYPE: PRT
<213> ORGANISM: Rhinovirus C10

<400> SEQUENCE: 24

Lys His Phe Leu Glu His Arg Ala Asp Ile Thr Thr Leu
1               5                   10

<210> SEQ ID NO 25
<211> LENGTH: 12
<212> TYPE: PRT
<213> ORGANISM: Rhinovirus C11

<400> SEQUENCE: 25

Arg Lys Val Ser Asp Asp Ser Thr Leu Thr Arg
1               5                   10

<210> SEQ ID NO 26
<211> LENGTH: 13
<212> TYPE: PRT
<213> ORGANISM: Rhinovirus C11

<400> SEQUENCE: 26

Asp His Tyr Ile Glu Thr Arg Ala Ser Val Lys Thr Ala
1               5                   10

<210> SEQ ID NO 27
<211> LENGTH: 13
<212> TYPE: PRT
<213> ORGANISM: Rhinovirus C12

<400> SEQUENCE: 27

Tyr Arg Thr Gly Thr Glu Gly Asn Tyr Thr Leu Lys Asn
1               5                   10

<210> SEQ ID NO 28
<211> LENGTH: 13
<212> TYPE: PRT
<213> ORGANISM: Rhinovirus C12

<400> SEQUENCE: 28

Arg His Phe Ile Gln His Arg Asn Asn Ile Lys Gly Leu
1               5                   10

<210> SEQ ID NO 29
<211> LENGTH: 4
<212> TYPE: PRT
<213> ORGANISM: Rhinovirus C

<400> SEQUENCE: 29

Val Asn Tyr Asn
1

<210> SEQ ID NO 30
<211> LENGTH: 12
<212> TYPE: PRT
<213> ORGANISM: Rhinovirus C13

<400> SEQUENCE: 30

Ile Ala Lys Pro Asn Ser Gly Gly Leu Leu Glu Gln
1               5                   10
```

```
<210> SEQ ID NO 31
<211> LENGTH: 13
<212> TYPE: PRT
<213> ORGANISM: Rhinovirus C13

<400> SEQUENCE: 31

Lys His Phe Leu Lys His Arg Pro Asp Ile Lys Ser Ala
1               5                   10

<210> SEQ ID NO 32
<211> LENGTH: 4
<212> TYPE: PRT
<213> ORGANISM: Rhinovirus C

<400> SEQUENCE: 32

Pro Asn Tyr His
1

<210> SEQ ID NO 33
<211> LENGTH: 12
<212> TYPE: PRT
<213> ORGANISM: Rhinovirus C14

<400> SEQUENCE: 33

Thr Thr Ala Pro Glu Gly Gly Gly Leu Leu Lys Glu
1               5                   10

<210> SEQ ID NO 34
<211> LENGTH: 13
<212> TYPE: PRT
<213> ORGANISM: Rhinovirus C14

<400> SEQUENCE: 34

Glu His Tyr Phe Lys Phe Arg Glu Asn Ile Lys Thr Ala
1               5                   10

<210> SEQ ID NO 35
<211> LENGTH: 13
<212> TYPE: PRT
<213> ORGANISM: Rhinovirus 15a

<400> SEQUENCE: 35

Arg His Phe Ile Lys Thr Arg Pro Leu Ile Ser Ser Ala
1               5                   10

<210> SEQ ID NO 36
<211> LENGTH: 15
<212> TYPE: PRT
<213> ORGANISM: Rhinovirus 15

<400> SEQUENCE: 36

Tyr Lys Pro Asn Ser Ser Gly Pro Asp Gln His Val Leu Glu Asp
1               5                   10                  15

<210> SEQ ID NO 37
<211> LENGTH: 13
<212> TYPE: PRT
<213> ORGANISM: Rhinovirus 15

<400> SEQUENCE: 37

Arg His Phe Ile Lys Thr Arg Pro His Ile Ser Ser Ala
1               5                   10
```

```
<210> SEQ ID NO 38
<211> LENGTH: 12
<212> TYPE: PRT
<213> ORGANISM: Rhinovirus C15

<400> SEQUENCE: 38

Tyr Lys Pro Asn Ala Asp Glu His Ile Leu Glu Asp
1               5                   10

<210> SEQ ID NO 39
<211> LENGTH: 13
<212> TYPE: PRT
<213> ORGANISM: Rhinovirus C15

<400> SEQUENCE: 39

Arg His Phe Ile Lys Thr Arg Pro Leu Ile Ser Ser Ala
1               5                   10

<210> SEQ ID NO 40
<211> LENGTH: 12
<212> TYPE: PRT
<213> ORGANISM: Rhinovirus C17

<400> SEQUENCE: 40

Val Pro Asp Ser Asn Glu Thr Asp Gly Leu Lys Glu
1               5                   10

<210> SEQ ID NO 41
<211> LENGTH: 13
<212> TYPE: PRT
<213> ORGANISM: Rhinovirus C17

<400> SEQUENCE: 41

Lys His Phe Ile Lys Pro Arg Glu His Ile Lys Asn Val
1               5                   10

<210> SEQ ID NO 42
<211> LENGTH: 12
<212> TYPE: PRT
<213> ORGANISM: Rhinovirus C18

<400> SEQUENCE: 42

Tyr Lys Glu Glu Glu Ser Glu Gln Asn Leu Lys Asp
1               5                   10

<210> SEQ ID NO 43
<211> LENGTH: 13
<212> TYPE: PRT
<213> ORGANISM: Rhinovirus C18

<400> SEQUENCE: 43

Arg His Phe Met Glu Phe Arg Arg Glu Ile Lys Thr Thr
1               5                   10

<210> SEQ ID NO 44
<211> LENGTH: 12
<212> TYPE: PRT
<213> ORGANISM: Rhinovirus C18

<400> SEQUENCE: 44

Lys Glu Glu Asn Glu Ser Glu Gln Asn Leu Lys Asp
1               5                   10
```

```
<210> SEQ ID NO 45
<211> LENGTH: 13
<212> TYPE: PRT
<213> ORGANISM: Rhinovirus C18

<400> SEQUENCE: 45

Arg His Phe Met Glu Phe Arg Arg Glu Ile Lys Thr Thr
1               5                   10

<210> SEQ ID NO 46
<211> LENGTH: 11
<212> TYPE: PRT
<213> ORGANISM: Rhinovirus C19

<400> SEQUENCE: 46

Thr Lys Val Asn Asp Thr Gln Val Leu Lys Glu
1               5                   10

<210> SEQ ID NO 47
<211> LENGTH: 13
<212> TYPE: PRT
<213> ORGANISM: Rhinovirus C19

<400> SEQUENCE: 47

Glu His Tyr Ile Lys Phe Arg Glu Ser Pro Arg Thr Ile
1               5                   10

<210> SEQ ID NO 48
<211> LENGTH: 15
<212> TYPE: PRT
<213> ORGANISM: Rhinovirus C20

<400> SEQUENCE: 48

Lys Lys Lys Val Pro Thr Asp Pro Asn Asn His Glu Leu Thr Lys
1               5                   10                  15

<210> SEQ ID NO 49
<211> LENGTH: 13
<212> TYPE: PRT
<213> ORGANISM: Rhinovirus C20

<400> SEQUENCE: 49

Val His Phe Leu Lys Pro Arg Thr Glu Ile Lys Thr Thr
1               5                   10

<210> SEQ ID NO 50
<211> LENGTH: 12
<212> TYPE: PRT
<213> ORGANISM: Rhinovirus C21

<400> SEQUENCE: 50

Ser Val Lys Ser Gly Thr Leu Asn Asp Leu Glu Gln
1               5                   10

<210> SEQ ID NO 51
<211> LENGTH: 13
<212> TYPE: PRT
<213> ORGANISM: Rhinovirus C21

<400> SEQUENCE: 51

Lys His Phe Leu Thr His Arg Pro Asp Ile Thr Thr Ala
1               5                   10
```

```
<210> SEQ ID NO 52
<211> LENGTH: 12
<212> TYPE: PRT
<213> ORGANISM: Rhinovirus C22

<400> SEQUENCE: 52

Asn Val Lys Asp Gln Gly Thr Lys Ala Leu Glu Gln
1               5                   10

<210> SEQ ID NO 53
<211> LENGTH: 13
<212> TYPE: PRT
<213> ORGANISM: Rhinovirus C22

<400> SEQUENCE: 53

Lys His Phe Leu Val Ser Arg Thr Asp Ile Lys Asn Val
1               5                   10

<210> SEQ ID NO 54
<211> LENGTH: 12
<212> TYPE: PRT
<213> ORGANISM: Rhinovirus C23

<400> SEQUENCE: 54

Tyr Lys Ala Asp Asp Asn Thr Ser Thr Leu Thr Asp
1               5                   10

<210> SEQ ID NO 55
<211> LENGTH: 13
<212> TYPE: PRT
<213> ORGANISM: Rhinovirus C23

<400> SEQUENCE: 55

Arg His Phe Leu Thr Pro Arg Asp Thr Ile Thr Thr Ala
1               5                   10

<210> SEQ ID NO 56
<211> LENGTH: 4
<212> TYPE: PRT
<213> ORGANISM: Rhinovirus C

<400> SEQUENCE: 56

Thr Asn Tyr Tyr
1

<210> SEQ ID NO 57
<211> LENGTH: 12
<212> TYPE: PRT
<213> ORGANISM: Rhinovirus C24

<400> SEQUENCE: 57

Phe Lys Ser Lys Glu Asn Glu Asn Ile Leu Val Pro
1               5                   10

<210> SEQ ID NO 58
<211> LENGTH: 13
<212> TYPE: PRT
<213> ORGANISM: Rhinovirus C24

<400> SEQUENCE: 58

Lys His Phe Ile Lys Pro Arg Ala Asn Ile Lys Asn Val
1               5                   10
```

-continued

```
<210> SEQ ID NO 59
<211> LENGTH: 12
<212> TYPE: PRT
<213> ORGANISM: Rhinovirus C25

<400> SEQUENCE: 59

Tyr Lys Pro Asp Gly Glu Gly His Ala Leu Thr Asp
1               5                   10

<210> SEQ ID NO 60
<211> LENGTH: 13
<212> TYPE: PRT
<213> ORGANISM: Rhinovirus C25

<400> SEQUENCE: 60

Arg His Phe Ile Gln Lys Arg Asn Asn Ile Lys Asn Val
1               5                   10

<210> SEQ ID NO 61
<211> LENGTH: 11
<212> TYPE: PRT
<213> ORGANISM: Rhinovirus C26

<400> SEQUENCE: 61

Thr Lys Ala Asp Glu Ser Gly Asn Leu Lys Glu
1               5                   10

<210> SEQ ID NO 62
<211> LENGTH: 13
<212> TYPE: PRT
<213> ORGANISM: Rhinovirus C26

<400> SEQUENCE: 62

Glu His Tyr Phe Arg Phe Arg Arg Asp Ile Lys Gly Ile
1               5                   10

<210> SEQ ID NO 63
<211> LENGTH: 10
<212> TYPE: PRT
<213> ORGANISM: Rhinovirus C27

<400> SEQUENCE: 63

Arg Lys Leu Ala Asp Asn Thr Leu Lys Val
1               5                   10

<210> SEQ ID NO 64
<211> LENGTH: 13
<212> TYPE: PRT
<213> ORGANISM: Rhinovirus C27

<400> SEQUENCE: 64

Asp His Tyr Ile Thr Thr Arg Pro Thr Val Lys Thr Ala
1               5                   10

<210> SEQ ID NO 65
<211> LENGTH: 13
<212> TYPE: PRT
<213> ORGANISM: Rhinovirus C28

<400> SEQUENCE: 65

Tyr Lys Glu Lys Asp Ala Ser Glu Asp Thr Leu Lys Ser
1               5                   10
```

```
<210> SEQ ID NO 66
<211> LENGTH: 13
<212> TYPE: PRT
<213> ORGANISM: Rhinovirus C28

<400> SEQUENCE: 66

Arg His Phe Met Glu Phe Arg Thr Ala Ile Lys Asn Val
1               5                   10

<210> SEQ ID NO 67
<211> LENGTH: 12
<212> TYPE: PRT
<213> ORGANISM: Rhinovirus C29

<400> SEQUENCE: 67

Arg Lys Val Arg Asp Asp Ser His Asp Leu Glu Lys
1               5                   10

<210> SEQ ID NO 68
<211> LENGTH: 13
<212> TYPE: PRT
<213> ORGANISM: Rhinovirus C29

<400> SEQUENCE: 68

Thr His Phe Ile Lys Thr Arg Asn Ser Ile Lys Thr Ala
1               5                   10

<210> SEQ ID NO 69
<211> LENGTH: 13
<212> TYPE: PRT
<213> ORGANISM: Rhinovirus C29

<400> SEQUENCE: 69

Val His Phe Leu Lys Pro Arg Thr Glu Ile Lys Thr Thr
1               5                   10

<210> SEQ ID NO 70
<211> LENGTH: 4
<212> TYPE: PRT
<213> ORGANISM: Rhinovirus C

<400> SEQUENCE: 70

Thr Asn Tyr Pro
1

<210> SEQ ID NO 71
<211> LENGTH: 12
<212> TYPE: PRT
<213> ORGANISM: Rhinovirus C30

<400> SEQUENCE: 71

Tyr Lys Ala Asn Asp Thr Ser Pro Leu Glu Asp Val
1               5                   10

<210> SEQ ID NO 72
<211> LENGTH: 13
<212> TYPE: PRT
<213> ORGANISM: Rhinovirus C30

<400> SEQUENCE: 72

Arg His Phe Ile Lys Thr Arg Asn Pro Ile Trp Asn Val
1               5                   10
```

<210> SEQ ID NO 73
<211> LENGTH: 12
<212> TYPE: PRT
<213> ORGANISM: Rhinovirus C31

<400> SEQUENCE: 73

Tyr Lys Ala Pro Gly Asn Ala Gln Glu Leu Lys Asp
1               5                   10

<210> SEQ ID NO 74
<211> LENGTH: 12
<212> TYPE: PRT
<213> ORGANISM: Rhinovirus C31

<400> SEQUENCE: 74

Arg His Phe Met Gln Phe Arg Lys Gln Ile Lys Asn
1               5                   10

<210> SEQ ID NO 75
<211> LENGTH: 13
<212> TYPE: PRT
<213> ORGANISM: Rhinovirus C32

<400> SEQUENCE: 75

Ile Pro Lys Thr Gly Ser Thr Thr Ser Glu Leu Glu Gln
1               5                   10

<210> SEQ ID NO 76
<211> LENGTH: 13
<212> TYPE: PRT
<213> ORGANISM: Rhinovirus C32

<400> SEQUENCE: 76

Lys His Phe Leu Ile Pro Arg Glu Asp Ile Lys Asn Val
1               5                   10

<210> SEQ ID NO 77
<211> LENGTH: 4
<212> TYPE: PRT
<213> ORGANISM: Rhinovirus C

<400> SEQUENCE: 77

Pro Asn Tyr His
1

<210> SEQ ID NO 78
<211> LENGTH: 12
<212> TYPE: PRT
<213> ORGANISM: Rhinovirus C33

<400> SEQUENCE: 78

Val Pro Ile Glu Gly Gly Ser Gly Asn Leu Lys Glu
1               5                   10

<210> SEQ ID NO 79
<211> LENGTH: 13
<212> TYPE: PRT
<213> ORGANISM: Rhinovirus C33

<400> SEQUENCE: 79

Glu His Tyr Phe Lys Phe Arg Asn Asp Ile Lys Ala Thr
1               5                   10

```
<210> SEQ ID NO 80
<211> LENGTH: 15
<212> TYPE: PRT
<213> ORGANISM: Rhinovirus C34

<400> SEQUENCE: 80

Lys Arg Lys Gln Pro Thr Asn Pro Asp Asn His Glu Leu Thr Lys
1               5                   10                  15

<210> SEQ ID NO 81
<211> LENGTH: 13
<212> TYPE: PRT
<213> ORGANISM: Rhinovirus C34

<400> SEQUENCE: 81

Val His Phe Leu Lys Pro Arg Pro Gly Asp Ser Ile Lys
1               5                   10

<210> SEQ ID NO 82
<211> LENGTH: 11
<212> TYPE: PRT
<213> ORGANISM: Rhinovirus C35

<400> SEQUENCE: 82

Val Asn Ile Gly Glu Thr Lys Glu Leu Thr Glu
1               5                   10

<210> SEQ ID NO 83
<211> LENGTH: 13
<212> TYPE: PRT
<213> ORGANISM: Rhinovirus C35

<400> SEQUENCE: 83

Arg His Tyr Leu Lys Pro Arg Asp Asp Ile Thr Thr Val
1               5                   10

<210> SEQ ID NO 84
<211> LENGTH: 12
<212> TYPE: PRT
<213> ORGANISM: Rhinovirus C36

<400> SEQUENCE: 84

Thr Arg Thr Gly Glu Asn Asn Gly Thr Leu Glu Glu
1               5                   10

<210> SEQ ID NO 85
<211> LENGTH: 13
<212> TYPE: PRT
<213> ORGANISM: Rhinovirus C36

<400> SEQUENCE: 85

Lys His Tyr Ile Lys Thr Arg Thr Asn Ile Lys Thr Phe
1               5                   10

<210> SEQ ID NO 86
<211> LENGTH: 11
<212> TYPE: PRT
<213> ORGANISM: Rhinovirus C37

<400> SEQUENCE: 86

Ile Arg Asp Gly Asp Gln Gly Met Leu Lys Gln
1               5                   10
```

```
<210> SEQ ID NO 87
<211> LENGTH: 13
<212> TYPE: PRT
<213> ORGANISM: Rhinovirus C37

<400> SEQUENCE: 87

Lys His Tyr Phe Lys Tyr Arg Asp Asp Ile Lys Asn Phe
1               5                   10

<210> SEQ ID NO 88
<211> LENGTH: 11
<212> TYPE: PRT
<213> ORGANISM: Rhinovirus C38

<400> SEQUENCE: 88

Arg Arg Val Tyr Pro Asp Ser Ala Asp Ser Thr
1               5                   10

<210> SEQ ID NO 89
<211> LENGTH: 13
<212> TYPE: PRT
<213> ORGANISM: Rhinovirus C38

<400> SEQUENCE: 89

Lys His Tyr Ile Thr Thr Arg Glu Ser Ile Lys Thr Ala
1               5                   10

<210> SEQ ID NO 90
<211> LENGTH: 14
<212> TYPE: PRT
<213> ORGANISM: Rhinovirus C38

<400> SEQUENCE: 90

Arg Arg Val Tyr Pro Asp Ser Ala Asp Ser Thr Leu Thr Lys
1               5                   10

<210> SEQ ID NO 91
<211> LENGTH: 13
<212> TYPE: PRT
<213> ORGANISM: Rhinovirus C38

<400> SEQUENCE: 91

Asp His Tyr Ile Thr Thr Arg Glu Ser Ile Lys Thr Ala
1               5                   10

<210> SEQ ID NO 92
<211> LENGTH: 13
<212> TYPE: PRT
<213> ORGANISM: Rhinovirus C39

<400> SEQUENCE: 92

Val Ile Lys Thr Gly Thr Thr Thr Gly Glu Leu Glu Gln
1               5                   10

<210> SEQ ID NO 93
<211> LENGTH: 13
<212> TYPE: PRT
<213> ORGANISM: Rhinovirus C39

<400> SEQUENCE: 93

Lys His Phe Leu Val Ala Arg Pro Asp Ile Lys Asn Val
1               5                   10
```

```
<210> SEQ ID NO 94
<211> LENGTH: 11
<212> TYPE: PRT
<213> ORGANISM: Rhinovirus C40

<400> SEQUENCE: 94

Thr Arg Lys Asn Asn Thr Ser Glu Leu Glu Glu
1               5                   10

<210> SEQ ID NO 95
<211> LENGTH: 13
<212> TYPE: PRT
<213> ORGANISM: Rhinovirus C40

<400> SEQUENCE: 95

Lys His Tyr Ile Lys Thr Arg Glu Thr Ile Lys Thr Ala
1               5                   10

<210> SEQ ID NO 96
<211> LENGTH: 11
<212> TYPE: PRT
<213> ORGANISM: Rhinovirus C41

<400> SEQUENCE: 96

Tyr Lys Ala Asp Glu Asn Ser Pro Leu Lys Asp
1               5                   10

<210> SEQ ID NO 97
<211> LENGTH: 13
<212> TYPE: PRT
<213> ORGANISM: Rhinovirus C41

<400> SEQUENCE: 97

Arg His Phe Ile Thr Thr Arg Glu Ser Ile Lys Asn Val
1               5                   10

<210> SEQ ID NO 98
<211> LENGTH: 8
<212> TYPE: PRT
<213> ORGANISM: Rhinovirus C42

<400> SEQUENCE: 98

Tyr Lys Lys Gly Asp Ala Leu Glu
1               5

<210> SEQ ID NO 99
<211> LENGTH: 13
<212> TYPE: PRT
<213> ORGANISM: Rhinovirus C42

<400> SEQUENCE: 99

Arg His Phe Ile His Thr Arg His Ile Lys Ile Leu
1               5                   10

<210> SEQ ID NO 100
<211> LENGTH: 14
<212> TYPE: PRT
<213> ORGANISM: Rhinovirus C42

<400> SEQUENCE: 100

Tyr Lys Lys Glu Asp Thr Thr Leu Glu Asp Arg His Phe Ile
1               5                   10
```

```
<210> SEQ ID NO 101
<211> LENGTH: 12
<212> TYPE: PRT
<213> ORGANISM: Rhinovirus C42

<400> SEQUENCE: 101

Gln His Arg Asp Gly Ile Lys Ile Leu Gln Asn Ala
1               5                   10

<210> SEQ ID NO 102
<211> LENGTH: 12
<212> TYPE: PRT
<213> ORGANISM: Rhinovirus C43

<400> SEQUENCE: 102

Lys Ile Lys Val Glu Ala Thr Lys Glu Leu Glu Gln
1               5                   10

<210> SEQ ID NO 103
<211> LENGTH: 13
<212> TYPE: PRT
<213> ORGANISM: Rhinovirus C43

<400> SEQUENCE: 103

Lys His Phe Leu Lys Pro Arg Gln Asp Ile Arg Asn Val
1               5                   10

<210> SEQ ID NO 104
<211> LENGTH: 12
<212> TYPE: PRT
<213> ORGANISM: Rhinovirus C43

<400> SEQUENCE: 104

Lys Ile Lys Val Glu Thr Thr Lys Glu Leu Glu Gln
1               5                   10

<210> SEQ ID NO 105
<211> LENGTH: 13
<212> TYPE: PRT
<213> ORGANISM: Rhinovirus C43

<400> SEQUENCE: 105

Lys His Phe Leu Lys Pro Arg Gln Asp Ile Arg Asn Ala
1               5                   10

<210> SEQ ID NO 106
<211> LENGTH: 13
<212> TYPE: PRT
<213> ORGANISM: Rhinovirus C44

<400> SEQUENCE: 106

Phe Lys Thr Val His Glu Gly Lys Asn Ile Leu Lys Asp
1               5                   10

<210> SEQ ID NO 107
<211> LENGTH: 13
<212> TYPE: PRT
<213> ORGANISM: Rhinovirus C44

<400> SEQUENCE: 107

Arg His Phe Ile Ile Pro Arg Ser Asn Ile Leu Gly Leu
1               5                   10
```

```
<210> SEQ ID NO 108
<211> LENGTH: 12
<212> TYPE: PRT
<213> ORGANISM: Rhinovirus C45

<400> SEQUENCE: 108

Arg Lys Val Asn Glu Thr Thr Thr Asp Leu Thr Lys
1               5                   10

<210> SEQ ID NO 109
<211> LENGTH: 13
<212> TYPE: PRT
<213> ORGANISM: Rhinovirus C45

<400> SEQUENCE: 109

Arg His Tyr Ile Gln Lys Arg Thr Ser Val Lys Ser Ala
1               5                   10

<210> SEQ ID NO 110
<211> LENGTH: 12
<212> TYPE: PRT
<213> ORGANISM: Rhinovirus C45

<400> SEQUENCE: 110

Arg Glu Val Asn Glu Thr Thr Thr Asp Leu Thr Lys
1               5                   10

<210> SEQ ID NO 111
<211> LENGTH: 13
<212> TYPE: PRT
<213> ORGANISM: Rhinovirus C45

<400> SEQUENCE: 111

Arg His Tyr Ile Gln Lys Arg Thr Ser Val Lys Ser Ala
1               5                   10

<210> SEQ ID NO 112
<211> LENGTH: 12
<212> TYPE: PRT
<213> ORGANISM: Rhinovirus C46

<400> SEQUENCE: 112

Val Pro Thr Gln Ala Asn Asp Gly Thr Leu Glu Glu
1               5                   10

<210> SEQ ID NO 113
<211> LENGTH: 13
<212> TYPE: PRT
<213> ORGANISM: Rhinovirus C46

<400> SEQUENCE: 113

Arg His Tyr Phe Lys Phe Arg Gly Asp Ile Lys Thr Ala
1               5                   10

<210> SEQ ID NO 114
<211> LENGTH: 11
<212> TYPE: PRT
<213> ORGANISM: Rhinovirus C47

<400> SEQUENCE: 114

Thr Asn Lys Gly Thr Thr Thr Glu Leu Glu Glu
1               5                   10
```

```
<210> SEQ ID NO 115
<211> LENGTH: 13
<212> TYPE: PRT
<213> ORGANISM: Rhinovirus C47

<400> SEQUENCE: 115

Lys His Tyr Ile Lys Thr Arg Glu Ser Ile Lys Thr Val
1               5                   10

<210> SEQ ID NO 116
<211> LENGTH: 4
<212> TYPE: PRT
<213> ORGANISM: Rhinovirus C

<400> SEQUENCE: 116

Thr Asp Tyr His
1

<210> SEQ ID NO 117
<211> LENGTH: 12
<212> TYPE: PRT
<213> ORGANISM: Rhinovirus C48

<400> SEQUENCE: 117

Ile Pro Val Glu Gly Gly Ser Gly Gly Leu Arg Glu
1               5                   10

<210> SEQ ID NO 118
<211> LENGTH: 13
<212> TYPE: PRT
<213> ORGANISM: Rhinovirus C48

<400> SEQUENCE: 118

Arg His Tyr Phe Thr Phe Arg Glu Asp Ile Lys Thr Ala
1               5                   10

<210> SEQ ID NO 119
<211> LENGTH: 13
<212> TYPE: PRT
<213> ORGANISM: Rhinovirus C49

<400> SEQUENCE: 119

Val Lys Lys Pro Gly Asp Asp Thr Gly Leu Leu Ile Gln
1               5                   10

<210> SEQ ID NO 120
<211> LENGTH: 13
<212> TYPE: PRT
<213> ORGANISM: Rhinovirus C49

<400> SEQUENCE: 120

Lys His Phe Ile Lys Pro Arg Gly Asp Ile Lys Thr Ala
1               5                   10

<210> SEQ ID NO 121
<211> LENGTH: 12
<212> TYPE: PRT
<213> ORGANISM: Rhinovirus C50

<400> SEQUENCE: 121

Thr Lys Asn Ala Ser Asn Glu Asn Val Leu Glu Glu
1               5                   10
```

```
<210> SEQ ID NO 122
<211> LENGTH: 13
<212> TYPE: PRT
<213> ORGANISM: Rhinovirus C50

<400> SEQUENCE: 122

Lys His Tyr Met Lys His Arg Thr Asp Ile Lys Thr Ala
1               5                   10

<210> SEQ ID NO 123
<211> LENGTH: 11
<212> TYPE: PRT
<213> ORGANISM: Rhinovirus C51

<400> SEQUENCE: 123

Ile Lys Asp Gly Glu Gln Gly Met Leu Arg Gln
1               5                   10

<210> SEQ ID NO 124
<211> LENGTH: 13
<212> TYPE: PRT
<213> ORGANISM: Rhinovirus C51

<400> SEQUENCE: 124

Arg His Tyr Phe Lys His Arg Gly Asp Ile Lys Asn Leu
1               5                   10

<210> SEQ ID NO 125
<211> LENGTH: 12
<212> TYPE: PRT
<213> ORGANISM: Rhinovirus C54

<400> SEQUENCE: 125

Arg Lys Val Asn Ser Thr Ser His Asp Leu Thr Lys
1               5                   10

<210> SEQ ID NO 126
<211> LENGTH: 13
<212> TYPE: PRT
<213> ORGANISM: Rhinovirus C54

<400> SEQUENCE: 126

Thr His Phe Ile Lys Thr Arg Asp Ser Ile Lys Thr Ala
1               5                   10

<210> SEQ ID NO 127
<211> LENGTH: 11
<212> TYPE: PRT
<213> ORGANISM: Rhinovirus C55

<400> SEQUENCE: 127

Leu Pro Lys Glu Gly Ser Asn Asp Leu Thr Glu
1               5                   10

<210> SEQ ID NO 128
<211> LENGTH: 13
<212> TYPE: PRT
<213> ORGANISM: Rhinovirus C55

<400> SEQUENCE: 128

Lys His Tyr Leu Asp Ser Arg Asn Asp Ile Thr Thr Ala
1               5                   10
```

```
<210> SEQ ID NO 129
<211> LENGTH: 41
<212> TYPE: PRT
<213> ORGANISM: Rhinovirus C15

<400> SEQUENCE: 129

Ala Thr Gln Tyr Thr His Lys Tyr Ser Thr Asn Tyr His Tyr Lys Pro
1               5                   10                  15

Asn Ser Ser Gly Pro Asp Glu His Val Leu Lys Asp Arg His Phe Ile
            20                  25                  30

Lys Thr Arg Pro Leu Ile Ser Ser Ala
        35                  40

<210> SEQ ID NO 130
<211> LENGTH: 39
<212> TYPE: PRT
<213> ORGANISM: Rhinovirus C15

<400> SEQUENCE: 130

Val Lys Val Asn Val Gly Tyr Asp His Thr His Pro Gly Gln Ser Gly
1               5                   10                  15

His Gln Ile Arg Gly Pro Ser Gln Ser Asn Asp Arg Ser Gly Gly Lys
            20                  25                  30

Pro Asp Glu Asp Pro Leu Phe
            35
```